United States Patent [19]
Iino et al.

[11] Patent Number: 5,944,665
[45] Date of Patent: Aug. 31, 1999

[54] ULTRASONIC DIAGNOSTIC APPARATUS

[75] Inventors: Hiroshi Iino; Yasushi Hiraoka; Masahiro Takase; Mitsuhiro Takeda; Kouzo Tokuyama; Atsushi Kajiwara; Kazuhiko Nobunaga, all of Nishinomiya, Japan

[73] Assignee: Furuno Electric Co., Ltd., Hyogo-Ken, Japan

[21] Appl. No.: 09/051,168

[22] PCT Filed: Apr. 8, 1997

[86] PCT No.: PCT/JP97/02710

§ 371 Date: Apr. 3, 1998

§ 102(e) Date: Apr. 3, 1998

[87] PCT Pub. No.: WO98/05258

PCT Pub. Date: Dec. 2, 1998

[30] Foreign Application Priority Data

Aug. 5, 1996 [JP] Japan ..................................... 8-223134

[51] Int. Cl.⁶ .................................................... A61B 08/00
[52] U.S. Cl. ............................................................ 600/437
[58] Field of Search .................................... 600/437, 438, 600/459, 462, 472, 439

[56] References Cited

U.S. PATENT DOCUMENTS 5,749,363   5/1998   Ishii et al. ............................... 600/437

*Primary Examiner*—William E. Kamm
*Assistant Examiner*—Maulin Patel
*Attorney, Agent, or Firm*—Birch, Stewart, Kolasch & Birch

[57] ABSTRACT

An ultrasonic diagnostic apparatus for diagnosing a characteristic of a body to be examined by passing ultrasound through the body to be examined which is placed between a pair of ultrasound transducers.

The apparatus comprises a pair of ultrasound transducers which are fixedly disposed facing to one another, with one of the ultrasound transducers (5) having a first standoff on the transmitting/receiving surface thereof, with the other ultrasound transducer (4) being housed in a movable tank having a second standoff at its front end, and moves the movable tank so that the body between the front end surface of the first standoff and the front end surface of the second standoff are brought into contact thereto and diagnoses a characteristic of the body based on signals emitted and received by the ultrasound transducers.

18 Claims, 11 Drawing Sheets

FIG. 7

| CHECK ITEM \ ACCEPTABILITY | ACCEPTABLE | UNACCEPTABLE (FAULTY) |
|---|---|---|
| SIGNAL INTENSITY | (waveform) | (waveform) |
| WAVEFORM DISTORTION | (waveform) | (waveform) |
| STABILITY OVER TIME | (waveform) | (waveform) |

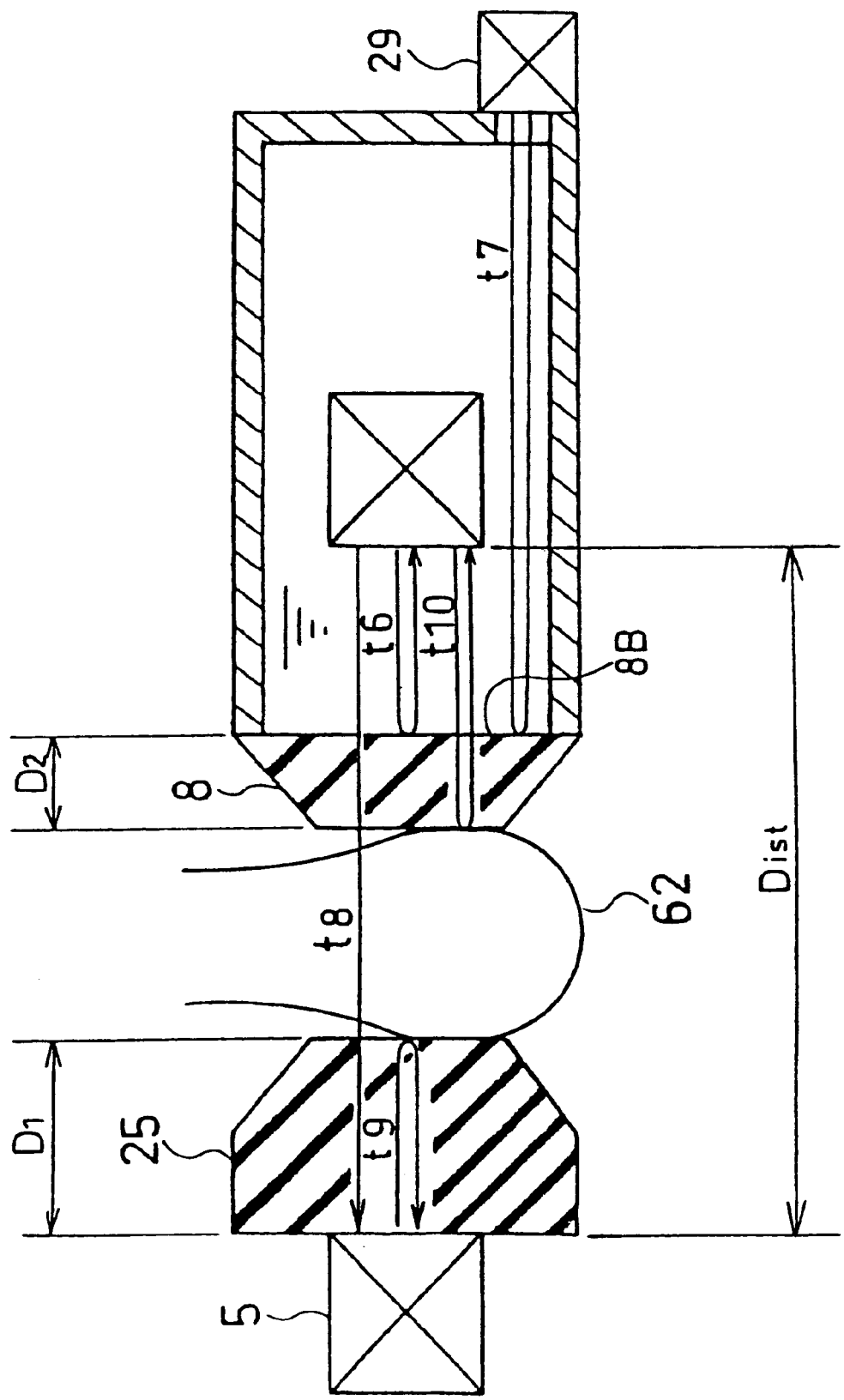

ULTRASONIC DIAGNOSTIC APPARATUS

This application claims the benefit under 35 U.S.C. §371 of prior PCT International Application No. PCT/JP97/02710, which has an International filing date of Apr. 8, 1997, which designated the United States of America, the entire contents of which are hereby incorporated by references.

TECHNICAL FIELD

The present invention relates to ultrasonic diagnostic apparatus utilized in diagnosing osteoporosis, for instance. More particularly, the invention relates to apparatus which obtain information on characteristics of a body part to be examined by producing sound waves which are passed through the body part positioned between a pair of transducers.

BACKGROUND ART

Osteoporosis is a symptom characterized by a decrease in the density of bone structures due to a lack of calcium, for instance. One method of diagnosing osteoporosis having been heretofore proposed is to quantitatively determine a bone characteristic (e.g., bone salt density) by passing ultrasonic waves through a bone and measuring the propagation speed of sound (SOS) in the bone. An ultrasonic examination of this kind is usually performed on a heel of the foot where the thickness of soft tissue is small.

A conventional apparatus (which is referred to as an ultrasonic bone-salt determination apparatus) for measuring the bone characteristics in the aforementioned fashion is movably mounted on a platform and, thus, makes use of a pair of movable parts with an ultrasound generator and an ultrasound detector installed face to face with each other individually on inside walls of the movable parts. A human heel is placed between the movable parts to interrupt a straight path between the ultrasound generator and detector, and the movable parts are repositioned such that the ultrasound generator and detector come in close contact with the heel in the air to permit propagation of ultrasonic waves. If ultrasound is emitted from the generator in this condition, it propagates at a speed that is dependent upon the bone salt content of the heel bone when passing through it. Thus, it is possible to measure a quantity corresponding to the bone salt content of the heel bone, which is the body part to be examined, by determining the speed of sound (SOS) of the ultrasound with the detector.

Specifically, the speed of sound (SOS) (SOS=L/T (m/s)) in the body part to be examined (heel) is derived from the distance L between the ultrasound generator and detector and the travel time T needed for a sound signal to propagate through the heel obtained by the ultrasound to pass through the body part to be examined (heel) as described above. The speed of sound (SOS) is converted into the corresponding bone salt content of the body part to be examined (heel) and, then, a judgment is made concerning the presence or absence of osteoporosis mentioned above. The apparatus intended for use in the above-described diagnosis is referred to as a dry-type ultrasonic diagnostic apparatus.

A pair of movable parts are used in the aforementioned dry-type ultrasonic diagnostic apparatus due to the need for holding the ultrasound generator and detector in close contact with the body part to be examined (heel). This arrangement, however, has made it essential to measure the aforesaid distance L (i.e., the distance L between the ultrasound generator and detector) each time a measurement is made by passing the ultrasound through the body part to be examined (heel). Further, it is necessary to move the individual movable parts by using a robust, precision mechanism and prepare an electric signal processing system featuring good linearity and high resolution for measuring the distance L with a high degree of accuracy. It has, however, been difficult to measure it with good accuracy, which results in an increase in the cost of the apparatus itself. Since it has been difficult to measure the distance L between the ultrasound generator and detector with good accuracy as stated above, the propagation speed of sound (SOS) determined would vary from one measurement to another or contain a significant error, rendering measurement results unreliable.

A previously proposed solution to the aforementioned problems is found in an ultrasonic diagnostic apparatus described in Japanese Unexamined Patent Publication No. 5-228148. This kind of apparatus employs a frame associated with an ultrasound generator and detector which are attached to the inside of the frame as well as a liquid-filling bag (bolus) provided within the frame. The bolus is filled with a matching liquid so that the body part to be examined (heel) is surrounded by the matching liquid without allowing any gaps around the body part. If ultrasound is emitted from the generator in this condition, it propagates at a speed dependent upon the bone salt content of the heel bone when passing through it. Thus, it is possible to measure a quantity corresponding to the bone salt content of the heel bone, which is the body part to be examined, by determining the speed of sound (SOS) of the ultrasound with the detector, and thereby make a judgment about the presence or absence of osteoporosis. The apparatus designed to diagnose in this manner is hereinafter referred to as a bolus-type ultrasonic diagnostic apparatus.

The distance L between the ultrasound generator and detector is fixed by attaching them to the inside of the frame as described above. With this arrangement, it becomes possible to eliminate variations in the propagation speed of sound (SOS) obtained in successive measurements and large errors in measurement results which would occur in the aforementioned dry-type ultrasonic diagnostic apparatus.

In the bolus-type ultrasonic diagnostic apparatus, however, propagation of the ultrasound up to the body part to be examined (heel) is ensured by filling the liquid-filling bag (bolus) with the matching liquid and thereby increasing the volume of the liquid-filling bag. For this reason, elastic fatigue of the liquid-filling bag (bolus) increases in proportion to the number of times it is used for measurement and diagnosis (i.e., the number of times the volume of the liquid-filling bag is increased and decreased), and this would potentially develop a problem concerning its durability. Especially because the liquid-filling bag is required to be able to wrap around the body part to be examined (heel) regardless of its physical size, any material used for making the liquid-filling bag must be flexible enough to provide a great dimensional coverage. Further, the material of the liquid-filling bag must be made thin enough to provide absolutely required ultrasound-transmitting properties.

Therefore, a material which would cause deterioration of the liquid-filling bag (bolus) and its fracture in a short time is not only useless but would develop such an accident that the matching liquid spilled out of the liquid-filling bag (bolus) adheres to the body part to be examined (heel). This will not pose any problem to the human heel if the matching liquid is water. Potential danger exists, however, because the matching liquid could contain chemicals, other than water, in certain cases for altering temperature response of ultrasound propagation velocity, or for preventing deterioration of the material, for instance.

Since the liquid-filling bag (bolus) is formed of a flexible and tough material, it may develop wrinkles as a matter of course when it is in service. Formation of such wrinkles in a surface that comes into contact with the body part to be examined (heel) would result in extremely abnormal transmission and reflection of ultrasonic waves, making it impossible to perform any measurement.

DISCLOSURE OF THE INVENTION

Accordingly, it is an object of the invention to provide an ultrasonic diagnostic apparatus which has excellent durability and safety features and a capability to obtain highly reliable results of diagnosis on a body part examined.

It is another object of the invention to provide a dry-type ultrasonic diagnostic apparatus featuring a simple mechanism and easy operation that can measure a characteristic of bone.

It is still another object of the invention to provide a dry-type ultrasonic diagnostic apparatus which can easily measure the width of a body part being examined.

It is yet another object of the invention to provide an ultrasonic diagnostic apparatus which is characterized in that a pair of ultrasound transmitting/receiving elements are immovably installed facing each other, a standoff is mounted at the front of a transmitting/receiving surface of one of the ultrasound transmitting/receiving elements, the other ultrasound transmitting/receiving element is housed in a movable tank fitted with a standoff at a forward end, and the movable tank is moved.

It is a further object of the invention to provide an ultrasonic diagnostic apparatus which is characterized in that a pair of ultrasound transmitting/receiving elements are immovably installed facing each other, a first standoff is mounted at the front of a transmitting/receiving surface of one of the ultrasound transmitting/receiving elements, the other ultrasound transmitting/receiving element is housed in a movable tank fitted with a second standoff at a forward end, the movable tank is moved such that a front end surface of the first standoff and a front end surface of the second standoff are pushed against a body part to be examined which is located between the two front end surfaces, and the apparatus diagnoses a characteristic of the body part to be examined based on signals transmitted and received by the ultrasound transmitting/receiving elements.

It is a still further object of the invention to provide an ultrasonic diagnostic apparatus which is characterized in that a pair of ultrasound transmitting/receiving elements are immovably installed facing each other, a first standoff is mounted at the front of a transmitting/receiving surface of one of the ultrasound transmitting/receiving elements, the other ultrasound transmitting/receiving element is housed in a movable tank fitted with a second standoff at a forward end, the movable tank is moved such that a front end surface of the first standoff and a front end surface of the second standoff are pushed against a body part to be examined which is located between the two front end surfaces, and the SOS is calculated based on signals transmitted and received by the pair of ultrasound transmitting/receiving elements.

What is claimed in claim 1 of the invention is an ultrasonic diagnostic apparatus for diagnosing a characteristic of a body part to be examined by passing ultrasound through the body part to be examined, the ultrasonic diagnostic apparatus comprising a platform on which the body part to be examined is loaded, a pair of measuring units mounted on the platform, at least one of the measuring units being made movable so that the distance between them can be varied in accordance with the size of the body part to be examined whereby the ultrasound is allowed to pass through the body part to be examined and the measuring units can be pushed against it, an ultrasound-transmitting fluid filled in the measuring unit whichever is made movable, and a pair of ultrasound transmitting/receiving elements disposed individually in the pair of measuring units, wherein the ultrasound transmitting/receiving element housed in the measuring unit whichever is made movable is held in the ultrasound-transmitting fluid and sustained by the platform such that the distance between the ultrasound transmitting/receiving elements is fixed:

With this arrangement, the distance between the measuring units can be varied in accordance with the size of the body part to be examined so that they are pushed against the body part. It is then possible to measure the propagation time of ultrasound which is emitted from each ultrasound transmitting/receiving element and passed through, or reflected by, the body part to be examined, and determine the propagation speed of the ultrasound passing through the body part based on the propagation time and the speed of the ultrasound given by the temperature of the ultrasound-transmitting fluid, for instance. Further, the distance between the ultrasound transmitting/receiving elements is not changed whichever measuring unit is moved.

According to the invention of claim 1, the measuring units can be pushed against the body part to be examined by varying the distance between the them in accordance with the size of the body part, without varying the distance between the ultrasound transmitting/receiving elements even when the movable measuring unit is moved. A consequence of this is that it is no longer necessary to measure the distance between the individual ultrasound transmitting/receiving elements each time a characteristic of a body part to be examined is diagnosed, unlike the case with the prior art. Another consequence is that there is no risk of leakage of the ultrasound-transmitting fluid due to breakage of each measuring unit, because it is not necessary to make those portions which are brought into contact with the body part flexible. Furthermore, since it is not necessary to achieve matching between the body part to be examined and the ultrasound-transmitting fluid, the time required for diagnosing the characteristic of the body part can be shortened, and the apparatus can be made easy to maintain and reduced in size.

What is claimed in claim 2 of the invention is the apparatus of claim 1, in which the measuring unit whichever is made movable includes a standoff made of an ultrasound-transmitting solid which is pushed against the body part to be examined and a movable tank fitted with the standoff at a forward end, the movable tank holding the ultrasound-transmitting fluid and accommodating the ultrasound transmitting/receiving element, wherein a surface of the standoff closer to the movable tank is formed to act as a reflecting surface for the ultrasound emitted from the ultrasound transmitting/receiving element.

If the ultrasound transmitting/receiving element is fixed in the ultrasound-transmitting fluid as described above, it is possible to cause the ultrasound to pass through, or be reflected by, the body part to be examined through the ultrasound-transmitting fluid and the ultrasound-transmitting solid with reliability and good accuracy.

According to the invention of claim 2, the surface of the standoff closer to the movable tank is formed to act as a reflecting surface for the ultrasound emitted from the ultrasound transmitting/receiving element so that the positional relationship between the standoff and the ultrasound transmitting/receiving element can be accurately measured.

What is claimed in claim 3 of the invention is the apparatus of claim 2, in which the platform is provided with a guide mechanism extending in the moving direction of the movable tank, wherein the guide mechanism movably supports the movable tank and immovably supports the ultrasound transmitting/receiving element. The guide mechanism serves both to support the movable tank allowing its movements and to support the ultrasound transmitting/receiving element at a fixed position.

According to the invention of claim 3, the guide mechanism can be made in a simple construction as it serves a double function of movably supporting the movable tank and immovably supporting the ultrasound transmitting/receiving element.

What is claimed in claim 4 of the invention is the apparatus of claim 3, in which the guide mechanism has seal members fitted at least at two positions of the movable tank, a supporting point of the ultrasound transmitting/receiving element is located in a space sealed by the seal members, and the ultrasound-transmitting fluid in the movable tank is sealed off from outside air. With this arrangement, the ultrasound-transmitting fluid in the movable tank is sealed off.

According to the invention of claim 4, it is possible to make the whole apparatus easy to handle and prevent deterioration of the fluid, for instance, because the ultrasound-transmitting fluid in the movable tank is sealed off.

What is claimed in claim 5 of the invention is the apparatus of claim 4, in which the space sealed by the seal members is filled with the ultrasound-transmitting fluid. This makes it possible to choose the location of the guide mechanism regardless of the level of the liquid surface.

According to the invention of claim 5, it becomes possible to assemble the guide mechanism with the movable tank and reduce the overall size of the apparatus because the guide mechanism can be positioned regardless of the surface level of the ultrasound-transmitting fluid.

What is claimed in claim 6 of the invention is the apparatus of claim 2, in which a third ultrasound transmitting/receiving element is attached to the rear end of the movable tank in such a way that the third ultrasound transmitting/receiving element can emit ultrasound toward and receive it from the reflecting surface of the standoff. This makes it possible to calculate the positional relationship between the standoff and the earlier-mentioned ultrasound transmitting/receiving element from a comparison of transmission/reception of the ultrasound between the third ultrasound transmitting/receiving element and the reflecting surface and transmission/reception of the ultrasound between the ultrasound transmitting/receiving element and the reflecting surface whose positional relationship varies, without using the speed of the ultrasound derived from the temperature of the ultrasound-transmitting fluid in the movable tank.

According to the invention of claim 6, the third ultrasound transmitting/receiving element eliminates the need for measuring the temperature of the ultrasound-transmitting fluid, making it possible to accurately calculate the positional relationship between the standoff of the movable tank and the ultrasound transmitting/receiving element and thereby increase the accuracy of examination results.

What is claimed in claim 7 of the invention is the apparatus of claims 1 or 2, in which one of the pair of measuring units is fixed while the other is made movable. This makes it possible to push the measuring units against the body part to be examined only by moving the movable measuring unit relative to the fixed measuring unit.

According to the invention of claim 7, the measuring units can be pushed against the body part to be examined only by moving the movable measuring unit relative to the fixed measuring unit, and the apparatus can be reduced in size and simplified.

What is claimed in claim 8 of the invention is the apparatus of claim 7, in which the fixed measuring unit is formed of a standoff made of an ultrasound-transmitting solid which is pushed against the body part to be examined and the aforementioned ultrasound transmitting/receiving element is affixed to this standoff. This makes it possible to keep the standoff and the ultrasound transmitting/receiving element in close contact with each other.

According to the invention of claim 8, the standoff and the ultrasound transmitting/receiving element can be held in close contact with each other so that the construction of the standoff of the fixed side can be simplified.

What is claimed in claim 9 of the invention is the apparatus of claim 1, further comprising a controller for controlling the pair of measuring units, wherein the controller incorporates, in addition to measurement mode in which the propagation speed of the ultrasound passing through the body part to be examined is determined from the time required for the ultrasound to pass through the body part and the width of the body part, judgment mode in which a judgment is made as to whether the ultrasound passed through the body part is acceptable or unacceptable before determining its propagation speed through the body part and/or calibration mode in which an ultrasound-transmitting object of a known width is sandwiched between the pair of measuring units, or the pair of measuring units are brought into mutual contact, and the positional relationship between the measuring unit whichever is made movable and the ultrasound transmitting/receiving element housed in it is measured. It is possible to detect and annunciate an anomaly of contact between the measuring units and the body part to be examined based on a comparison of the ultrasound passed through the body part with at least such physical quantities as sound intensity, waveform and stability through lapse of time obtained by executing the judgment mode which is selected either automatically or manually. Further, the width of the body part to be examined can be calculated from a comparison with the width of the ultrasound-transmitting object known by executing the calibration mode which is selected by manual operation.

According to the invention of claim 9, it becomes possible to execute an appropriate examination through the choice of various modes. As an example, the judgment mode makes it possible to verify proper contact between the measuring units and the body part to be examined and obtain reliable measurement results. Further, the calibration mode makes it possible to calculate the width of the body part to be examined from a comparison with the known width of the ultrasound-transmitting object and thereby obtain accurate measurements regardless of changes of each standoff with the lapse of time which is pushed against the body part to be examined.

What is claimed in claim 10 of the invention is an ultrasonic diagnostic apparatus for diagnosing a characteristic of a body part to be examined by passing ultrasound through the body part to be examined, the ultrasonic diagnostic apparatus comprising a pair of ultrasound transmitting/receiving elements immovably installed facing each other to transmit and receive ultrasonic signals, a standoff mounted at the front of a transmitting/receiving surface of one of the ultrasound transmitting/receiving elements, a movable tank fitted with a standoff at a forward end, the movable tank holding an ultrasound-transmitting fluid and accommodating the other ultrasound transmitting/receiving element, and moving means for moving the movable tank either forward or backward.

This construction provides easy operation since the pair of ultrasound transmitting/receiving elements are immovably installed and only one standoff is allowed to move.

What is claimed in claim 11 of the invention is an ultrasonic diagnostic apparatus for diagnosing a characteristic of a body part to be examined by passing ultrasound through the body part to be examined, the ultrasonic diagnostic apparatus comprising a pair of ultrasound transmitting/receiving elements immovably installed facing each other to transmit and receive ultrasonic signals, a first standoff mounted at the front of a transmitting/receiving surface of one of the ultrasound transmitting/receiving elements, a movable tank fitted with a second standoff at a forward end, the movable tank holding an ultrasound-transmitting fluid and accommodating the other ultrasound transmitting/receiving element, moving means for moving the movable tank such that a front end surface of the first standoff and a front end surface of the second standoff are pushed against the body part to be examined which is located between the two front end surfaces, and processing means for calculating the SOS through the body part based on the signals transmitted and received by the pair of ultrasound transmitting/receiving elements.

It is possible to calculate the SOS with the apparatus which is easy to operate.

What is claimed in claim 12 of the invention is an ultrasonic diagnostic apparatus for diagnosing a characteristic of a body part to be examined by passing ultrasound through the body part to be examined, the ultrasonic diagnostic apparatus comprising a pair of ultrasound transmitting/receiving elements immovably installed facing each other to transmit and receive ultrasonic signals, a first standoff mounted at the front of a transmitting/receiving surface of one of the ultrasound transmitting/receiving elements, a movable tank fitted with a second standoff at a forward end, the movable tank holding an ultrasound-transmitting medium and accommodating the other ultrasound transmitting/receiving element, moving means for moving the movable tank such that a front end surface of the first standoff and a front end surface of the second standoff are pushed against the body part to be examined which is located between the two front end surfaces, width measuring means for measuring the width of the body part to be examined, transmission delay time measuring means for measuring the time required for an acoustic signal to pass through the body part to be examined, and processing means for calculating the SOS through the body part based on outputs of the width measuring means and the transmission delay time measuring means.

What is claimed in claim 13 of the invention is an ultrasonic diagnostic apparatus for diagnosing a characteristic of a body part to be examined by passing ultrasound through the body part to be examined, the ultrasonic diagnostic apparatus comprising first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, the second standoff having a front end surface and a rear end surface which are parallel to each other, the movable tank holding an ultrasound-transmitting fluid and accommodating the second ultrasound transmitting/receiving element, moving means for moving the movable tank such that the front end surface of the first standoff and the front end surface of the second standoff are pushed against a calibration phantom or the body part to be examined whichever located between the two front end surfaces, and processing means for performing a mathematical operation defined by the following equation based on signals transmitted and received by the first and second ultrasound transmitting/receiving elements:

$$SOS=(\text{width of body part})/(\text{travel time})=((\text{position of standoff during calibration})-(\text{position of standoff during measurement})+(\text{width of calibration phantom}))/((\text{transmission delay time})-(\text{reflection delay times on both sides})/2)=(F+V(Cr) \cdot t1-V(C) \cdot t3)/(t2-(t4+t5)/2)$$

where

F=width of phantom

V(C)=sound velocity in liquid at temperature C

V(Cr)=sound velocity in liquid at temperature Cr

C=temperature during measurement

Cr=temperature during calibration t1=period of time from transmission to reception of a signal emitted by the second ultrasound transmitting/receiving element and reflected by the rear end surface of the second standoff during calibration t2=period of time from transmission to reception of a signal emitted by the second ultrasound transmitting/receiving element and received by the first ultrasound transmitting/receiving element during measurement t3=period of time from transmission to reception of a signal emitted by the second ultrasound transmitting/receiving element and reflected by the rear end surface of the second standoff during measurement t4=period of time from transmission to reception of a signal emitted by the first ultrasound transmitting/receiving element and reflected by the front end surface of the first standoff during measurement t5=period of time from transmission to reception of a signal emitted by the second ultrasound transmitting/receiving element and reflected by the front end surface of the second standoff during measurement This makes it possible to perform accurate measurements even when the width of each standoff has changed with the lapse of time.

What is claimed in claim 14 of the invention is an ultrasonic diagnostic apparatus for diagnosing a characteristic of a body part to be examined by passing ultrasound through the body part to be examined, the ultrasonic diagnostic apparatus comprising first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, the second standoff having a front end surface and a rear end surface which are parallel to each other, the movable tank holding an ultrasound-transmitting fluid and accommodating the second ultrasound transmitting/receiving element, moving means for moving the movable tank such that the front end surface of the first standoff and the front end surface of the second standoff come into mutual contact during calibration or the front end surface of the first standoff and the front end surface of the second standoff are pushed against the body part to be examined which is located between the two front end surfaces during measurement, and processing means for performing a mathematical operation defined by the following equation based on signals transmitted and received by the first and second ultrasound transmitting/receiving elements:

$$SOS=(\text{width of body part})/(\text{travel time})=(V(Cr)\cdot t1-V(C)\cdot t3)/(t2-(t4+t5)/2)$$

where

V(C)=sound velocity in liquid at temperature C
V(Cr)=sound velocity in liquid at temperature Cr
C=temperature during measurement
Cr=temperature during calibration
t1=period of time from transmission to reception of a signal emitted by the second ultrasound transmitting/receiving element and reflected by the rear end surface of the second standoff during calibration
t2=period of time from transmission to reception of a signal emitted by the second ultrasound transmitting/receiving element and received by the first ultrasound transmitting/receiving element during measurement
t3=period of time from transmission to reception of a signal emitted by the second ultrasound transmitting/receiving element and reflected by the rear end surface of the second standoff during measurement
t4=period of time from transmission to reception of a signal emitted by the first ultrasound transmitting/receiving element and reflected by the front end surface of the first standoff during measurement
t5=period of time from transmission to reception of a signal emitted by the second ultrasound transmitting/receiving element and reflected by the front end surface of the second standoff during measurement This makes it possible to perform accurate measurements even when the phantom is not used.

What is claimed in claim 15 of the invention is an ultrasonic diagnostic apparatus for diagnosing a characteristic of a body part to be examined by passing ultrasound through the body part to be examined, the ultrasonic diagnostic apparatus comprising first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, the second standoff having a front end surface and a rear end surface which are parallel to each other, the movable tank holding an ultrasound-transmitting fluid and accommodating the second ultrasound transmitting/receiving element, a third ultrasound transmitting/receiving element installed at a read end of the movable tank, moving means for moving the movable tank such that the front end surface of the first standoff and the front end surface of the second standoff are pushed against a calibration phantom or the body part to be examined whichever located between the two front end surfaces, and processing means for performing a mathematical operation defined by the following equation based on signals transmitted and received by the first, second and third ultrasound transmitting/receiving elements:

$$SOS=(\text{width of body part})/(\text{travel time})=((\text{position of standoff during calibration})-(\text{position of standoff during measurement})+(\text{width of calibration phantom}))/((\text{transmission delay time})-(\text{reflection delay times on both sides})/2)=(F+L\cdot t1/t70-L\cdot t6/t7)/(t8-(t9+t10)/2)$$

where

F=width of phantom
L=length of movable tank
t1=period of time from transmission to reception of a signal emitted by the second ultrasound transmitting/receiving element and reflected by the rear end surface of the second standoff during calibration
t6=period of time from transmission to reception of a signal emitted by the second ultrasound transmitting/receiving element and reflected by the rear end surface of the second standoff during measurement
t7=period of time from transmission to reception of a signal emitted by the third ultrasound transmitting/receiving element and reflected by the rear end surface of the second standoff during measurement
t8=period of time from transmission to reception of a signal emitted by the second ultrasound transmitting/receiving element and received by the first ultrasound transmitting/receiving element during measurement
t9=period of time from transmission to reception of a signal emitted by the first ultrasound transmitting/receiving element and reflected by the front end surface of the first standoff during measurement
t10=period of time from transmission to reception of a signal emitted by the second ultrasound transmitting/receiving element and reflected by the front end surface of the second standoff during measurement
t70=period of time from transmission to reception of a signal emitted by the third ultrasound transmitting/receiving element and reflected by the rear end surface of the second standoff during calibration This makes it possible to perform accurate measurements without measuring the temperature of the ultrasound-transmitting fluid since the length of the movable tank is known.

What is claimed in claim 16 of the invention is an ultrasonic diagnostic apparatus for diagnosing a characteristic of a body part to be examined by passing ultrasound through the body part to be examined, the ultrasonic diagnostic apparatus comprising first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, the second standoff having a front end surface and a rear end surface which are parallel to each other, the movable tank holding an ultrasound-transmitting fluid and accommodating the second ultrasound transmitting/receiving element, moving means for moving the movable tank such that the front end surface of the first standoff and the front end surface of the second standoff are pushed against the body part to be examined which is located between the two front end surfaces, and processing means for performing a mathematical operation defined by the following equation based on signals transmitted and received by the first and second ultrasound transmitting/receiving elements:

$$SOS=(\text{width of body part})/(\text{travel time})=((\text{distance between probes})-(\text{width of standoffs})-(\text{travel distance through liquid}))/((\text{transmission delay time})-(\text{reflection delay times on both sides})/2)=(\text{Dist}-D1-D2-V(C)\cdot t3/2)/(t2-(t4+t5)/2)$$

where

Dist=distance between first and second ultrasound transmitting/receiving elements
D1=width of first standoff
D2=width of second standoff
V(C)=sound velocity in liquid at temperature C
C=temperature during measurement
t2=period of time from transmission to reception of a signal emitted by the second ultrasound transmitting/receiving element and received by the first ultrasound transmitting/receiving element
t3=period of time from transmission to reception of a signal emitted by the second ultrasound transmitting/receiving element and reflected by the rear end surface of the second standoff
t4=period of time from transmission to reception of a signal emitted by the first ultrasound transmitting/receiving element and reflected by the front end surface of the first standoff
t5=period of time from transmission to reception of a signal emitted by the second ultrasound transmitting/receiving element and reflected by the front end surface of the second standoff This makes it possible to perform measurements without executing the calibration mode.

What is claimed in claim 17 is an ultrasonic diagnostic apparatus for diagnosing a characteristic of a body part to be examined by passing ultrasound through the body part to be examined, the ultrasonic diagnostic apparatus comprising first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, the second standoff having a front end surface and a rear end surface which are parallel to each other, the movable tank holding an ultrasound-transmitting fluid and accommodating the second ultrasound transmitting/receiving element, a third ultrasound transmitting/receiving element installed at a read end of the movable tank, moving means for moving the movable tank such that the front end surface of the first standoff and the front end surface of the second standoff are pushed against the body part to be examined which is located between the two front end surfaces, and processing means for performing a mathematical operation defined by the following equation based on signals transmitted and received by the first, second and third ultrasound transmitting/receiving elements:

$$SOS=(\text{width of body part})/(\text{travel time})=(\text{Dist}-D1-D2-L\cdot t6/t7)/(t8-(t9+t10)/2)$$

where

Dist=distance between first and second ultrasound transmitting/receiving elements
D1=width of first standoff
D2=width of second standoff
t6=period of time from transmission to reception of a signal emitted by the second ultrasound transmitting/receiving element and reflected by the rear end surface of the second standoff
t7=period of time from transmission to reception of a signal emitted by the third ultrasound transmitting/receiving element and reflected by the rear end surface of the second standoff
t8=period of time from transmission to reception of a signal emitted by the second ultrasound transmitting/receiving element and received by the first ultrasound transmitting/receiving element
t9=period of time from transmission to reception of a signal emitted by the first ultrasound transmitting/receiving element and reflected by the front end surface of the first standoff
t10=period of time from transmission to reception of a signal emitted by the second ultrasound transmitting/receiving element and reflected by the front end surface of the second standoff This makes it possible to perform accurate measurements of the SOS without executing the calibration mode and without measuring the temperature of the ultrasound-transmitting fluid.

BRIEF DESCRIPTION OF THE DRAWINGS

FIG. 7 is a table showing items to be checked when judging whether or not measuring units are pushed against a body part to be examined in a satisfactory manner;

FIG. 11 is a schematic representation of a measuring condition in measurement mode performed by using a third ultrasound transmitting/receiving element but without employing calibration mode.

BEST MODES OF CARRYING OUT THE INVENTION

A method of ultrasonic diagnosis using an ultrasonic diagnostic apparatus according to specific embodiments of the invention is described below with reference to FIGS. 1 through 8.

Figure 1:
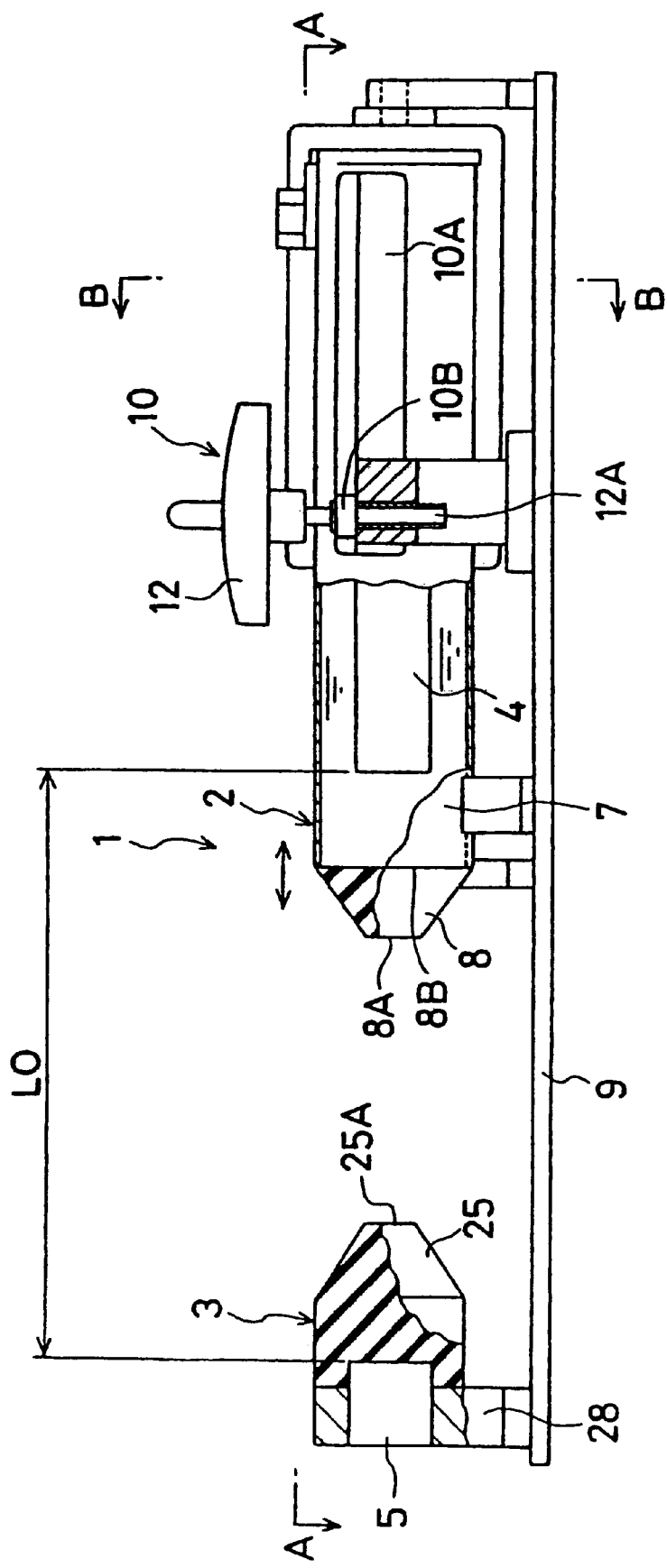
FIG. 1 is a side view showing the general construction of an ultrasonic diagnostic apparatus.
Figure 2:
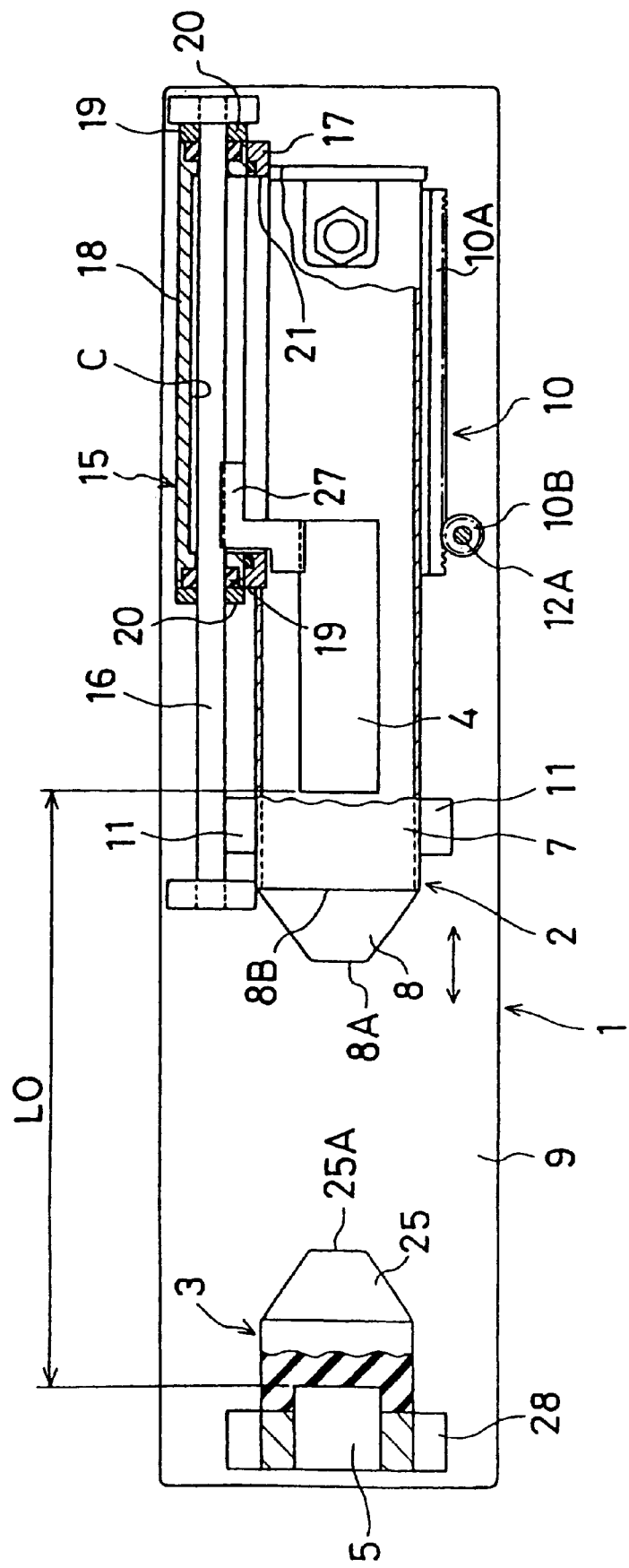
FIG. 2 is a sectional view taken along lines A—A of FIG. 1.
Figure 3:
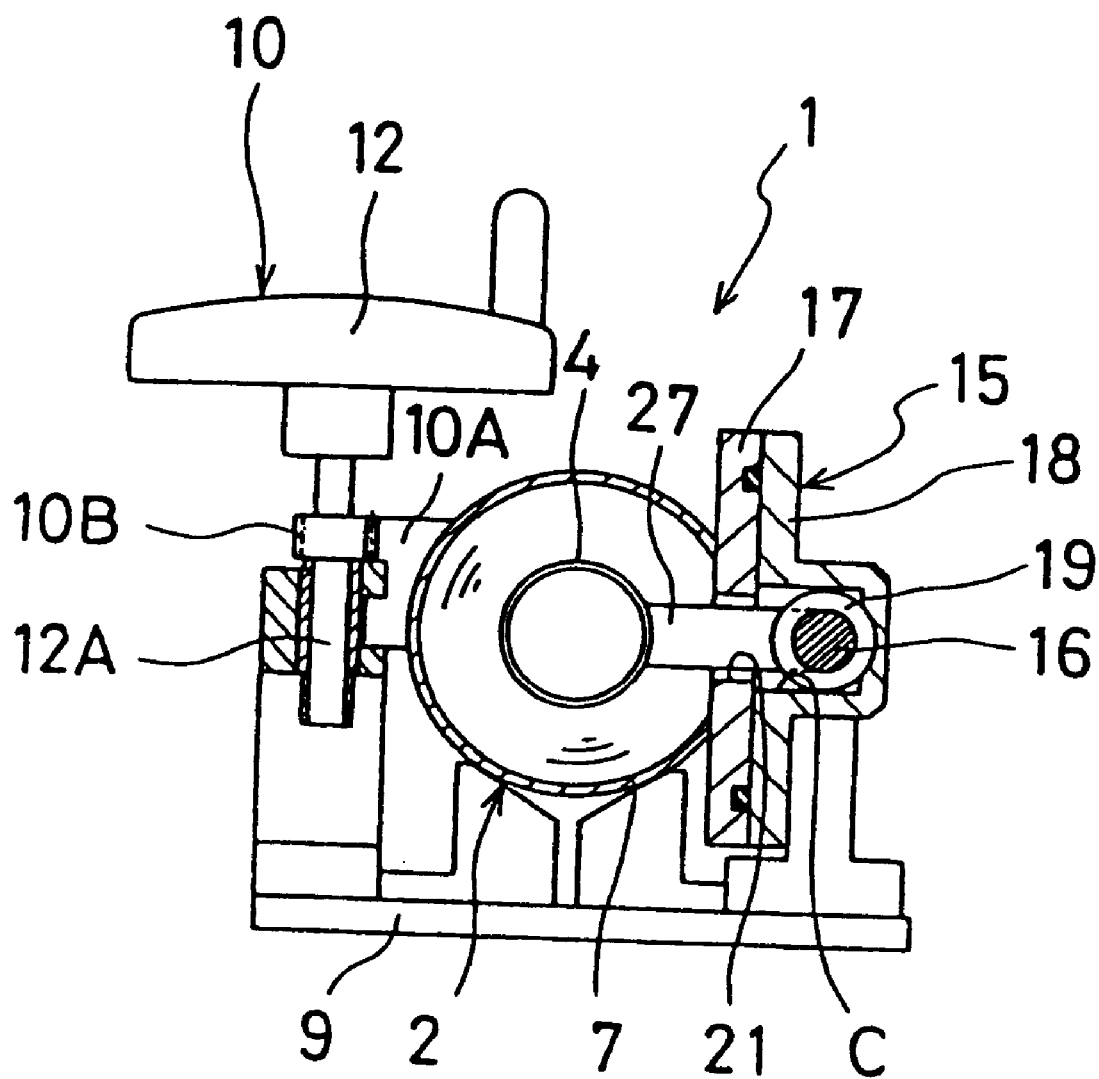
FIG. 3 is a sectional view taken along lines B—B of FIG. 1.

Referring first to FIGS. 1 through 3, the ultrasonic diagnostic apparatus of this embodiment is described.

In FIGS. 1 through 3, designated by the numeral 1 is an ultrasonic diagnostic apparatus comprising as its principal components a pair of measuring units 2, 3, a pair of ultrasound transmitting/receiving elements 4, 5 which are disposed within the respective measuring units 2, 3, and a controller 30 (shown in FIG. 5) which will be described later.

The measuring unit 2 includes a cylindrical movable tank 7 which is made movable to vary the distance from the facing measuring unit 3. The movable tank 7 has a sealed structure with a standoff 8 force-fitted at its forward end. The standoff 8 is pushed against a heel, which is a body part to be examined as will be described later, in the direction of the facing measuring unit 3. An ultrasound-transmitting fluid (e.g., water) which serves as an excellent ultrasound-transmitting substance for conducting ultrasonic signals emitted from the individual ultrasound transmitting/receiving elements 4, 5 is filled in a sealed internal space of the measuring unit 3. The diameter of the standoff 8 is gradually reduced to form a trapezoidal cross section projecting toward the measuring unit 3, and the standoff 8 has two reflecting surfaces 8A, 8B which are perpendicular to an axial direction of the movable tank 7. While various resin moldings are usable as the standoff 8, such as those made from acrylic resin, urethane and silicone which are good media for transmitting the ultrasonic signals and have a different acoustic impedance from the ultrasound-transmitting fluid (water), it is preferable to use a molded part of acrylic resin, a hard material which is less susceptible to deformation when pushed against the body part to be examined (heel).

The movable tank 7 of the measuring unit 2 is movably mounted on an examination table 9, on which the body part to be examined (hereinafter referred to simply as the heel) is placed, with a moving mechanism 10 fitted in between, and is supported by a pair of tank supports 11 which are located between the measuring unit 2 and the examination table 9, forming a V-groove. The moving mechanism 10 includes a pinion 10B which engages a rack 10A, which is fixed to the movable tank 7 and extends in the axial direction of the movable tank 7. The pinion 10B is fitted with a movable dial 12. The movable dial 12 has a dial shaft 12A rotatably fitted into an oilless bush of a supporting part 13 which is vertically mounted on the examination table 9. The pinion 10B is firmly fitted on the dial shaft 12A in such a way that the pinion 10B meshes with the rack 10A. The moving mechanism 10 further includes a retaining pin (not shown) which prohibits free rotation of the pinion 10B. With this arrangement, when the movable dial 12 is rotated in a forward or reverse turning direction, resultant rotary motion of the pinion 10B is transmitted to the rack 10A, causing the movable tank 7 (including the standoff 8) to produce a linear motion so that it will approaches, or recedes from, the measuring unit 3. The distance between the measuring unit 3 and the movable tank 7 can be varied in this manner, and the set distance between the measuring unit 2 and measuring unit 3 is maintained as the aforementioned retaining pin prohibits free rotation of the pinion 10B.

The aforementioned movable tank 7 is provided with a tank guide (guide mechanism) 15 extending parallel to its axial direction as shown in FIGS. 2 and 3. The tank guide 15 includes as its principal components a guide shaft 16 fixed to the fixed to the platform (examination table) 9, a guide cover 18 which is guided along the guide shaft 16, and seals 16, 19 fitted at both ends of the guide cover 18. The guide shaft 16 is supported by a pair of fixing parts which are vertically mounted on the platform (examination table) 9. The guide cover 18 is integrally assembled with a guide plate 17 which is fixed on the periphery of the movable tank 7 with seal members placed between the guide plate 17 and the guide cover 18 to achieve hermetic sealing, whereby the guide plate 17 and the guide cover 18 form as a whole a cylindrical guiding structure. The aforementioned guide shaft 16 is passed through a guide hole C formed by the aforementioned guide plate 17 and the guide cover 18, and the cylindrical guiding structure is supported by bearing portions at both ends of the guide cover 18 slidably along an axial direction of the guide shaft 16. Extending in the axial direction of the guide shaft 16, the guide hole C passes all the way between the side surfaces of the components 17 and 18. One each seal 19 and close-off plate 20 are fitted slidably around the guide shaft 16 in this order at each end of the guide hole C to close off the guide hole C from external air. The guide hole C is connected to the interior of the movable tank 7 through a connecting slot 21 formed in the guide plate 17, the connecting slot 21 extending in the axial direction of the guide shaft 16. This construction permits the guide hole C to be filled with the ultrasound-transmitting fluid.

Thus, when the movable tank 7 is moved by operating the moving mechanism 10 (rack 10A and pinion 10B) as described above, the seals 19 and the close-off plates 20 slide along the guide shaft 16 so that the movable tank 7 is guided in a stable manner as it approaches or recedes from the measuring unit 3. The individual seals 19 and the close-off plates 20 also serve to prevent leakage of the ultrasound-transmitting fluid (water) from inside the movable tank 7.

Figure 4:
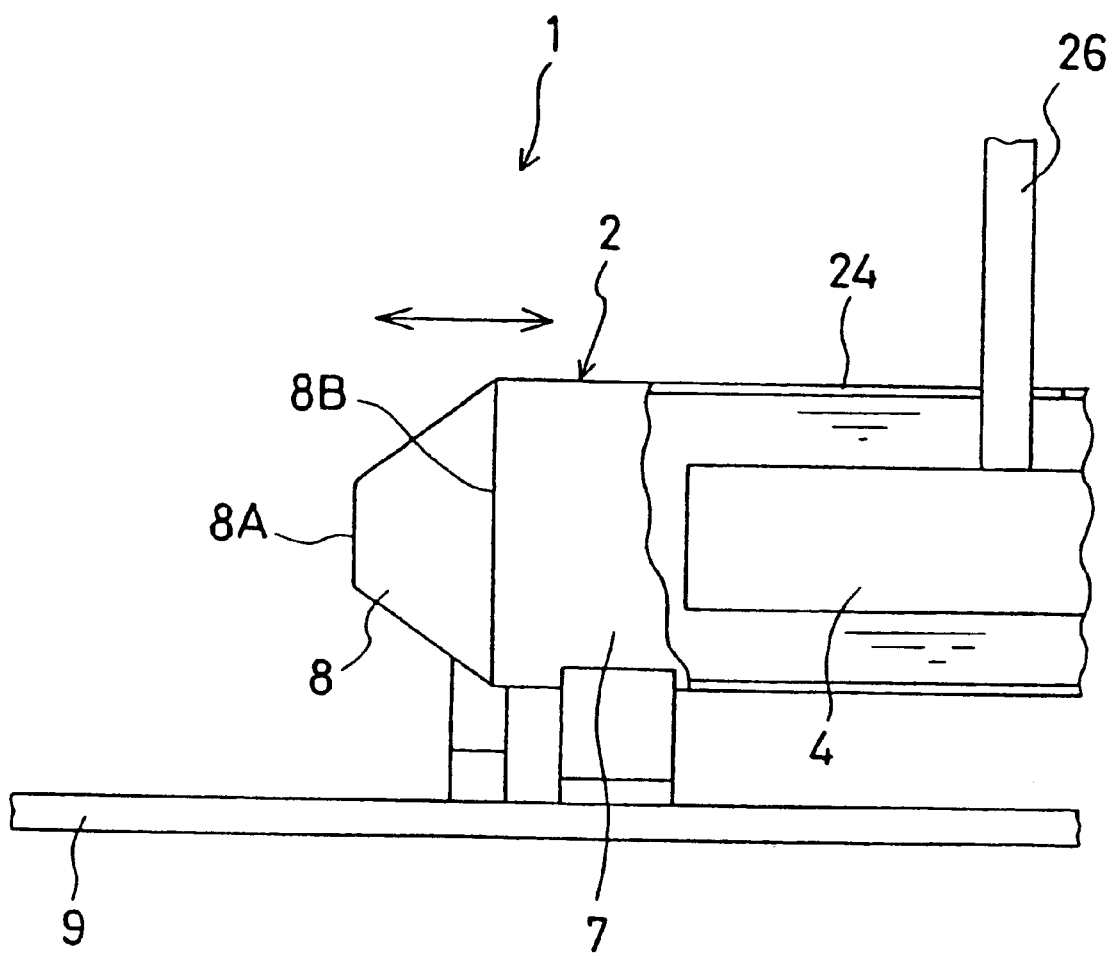
FIG. 4 is an enlarged fragmentary side view showing another embodiment of the ultrasonic diagnostic apparatus.

In the construction of the tank guide 15 for guiding the movable tank 7, if the amount of the ultrasound-transmitting fluid (water) filled in the movable tank 7 is not so large as to reach the guide hole C of the cylindrical guiding structure through the connecting slot 21, the ultrasound-transmitting fluid will not leak to the outside of the apparatus 1 even when both ends of the guide hole C are sealed by the seals 19 and the close-off plates 20. Moreover, the construction of the tank guide 15 is not limited to what is illustrated in FIGS. 1 to 3. In one alternative, a guide slot 24 extending in the moving direction of the movable tank 7 is formed at its top, and the ultrasound transmitting/receiving element 4 is fixed to a connecting member 26 which is inserted into the movable tank 7 through the guide slot 24, as shown in FIG. 4. As the connecting member 26 projecting through the guide slot 24 to the outside of the movable tank 7 is secured to an unillustrated fixing part, the ultrasound transmitting/receiving element 4 is held (fixed) in position in the ultrasound-transmitting fluid (water) while allowing movements of the movable tank 7. Since the movable tank 7 is not fully filled with the ultrasound-transmitting fluid, there is formed a surface of the liquid in an upper part of the movable tank 7.

Disposed face to face with the standoff 8 of the movable tank 7, the measuring unit 3 is essentially a standoff 25 formed of an ultrasound-transmitting solid having an excellent property for conducting the ultrasonic signals emitted from the individual ultrasound transmitting/receiving elements 4, 5. The diameter of the standoff 25 is gradually reduced to form a trapezoidal cross section projecting toward the standoff 8 of the movable tank 7, the standoff 25 has a reflecting surface 25A which is parallel to the reflecting surface 8A of the standoff 8. While various resin moldings are usable as the standoff 25, such as those made from acrylic resin, urethane and silicone which are good media for transmitting ultrasonic signals, it is preferable to use a molded part of acrylic resin, a hard material which is less susceptible to deformation when pushed against the heel, as is the case with the standoff 8 of the movable tank 7. The measuring unit 3 is firmly secured to a fixing base 28, which is vertically mounted on the aforementioned the platform (examination table) 9, with the axis of the standoff 25 aligned with the axis of the standoff 8 of the movable tank 7 and the reflecting surface 25A disposed parallel to the reflecting surface 8A. With this arrangement, the standoffs 8, 25 can be pushed against the heel in accordance with its size (or depending on differences in heel width) to sandwich and secure the heel on the examination table 9 with a linear motion of the movable tank 7 produced by the moving mechanism 10 as described above.

The standoff 8 of the movable tank 7 and the standoff 25 of a fixed tank 26 each have a trapezoidal cross section whose diameter gradually decreases toward their front ends as described above. This structure is used to partially sandwich the heel in securing it in position. This makes it easier to bring the standoffs 8, 25 in close contact with the body part being examined, such as heels of varying shapes.

A single device, which can both generate and detect ultrasonic signals and is usually called an ultrasonic transducer, is used as each of the ultrasound transmitting/receiving elements 4, 5 (hereinafter referred to as the transducers 4, 5). These ultrasonic transducers 4, 5 are disposed within the respective measuring units 2, 3 at a fixed distance LO from each other.

The transducer 4 is fixed in the ultrasound-transmitting fluid (water) within the standoff 8, facing the standoff 8, so that the transducer 4 can transmit and receive ultrasonic signals. Used for fixing the transducer 4 is a connecting member 27 which is secured to the aforementioned guide shaft 16. The connecting member 27 passes through the connecting slot 21 at right angle to the axial direction of the guide shaft 16 and sticks into the movable tank 7, and is fixed to the transducer 4. With the transducer 4 affixed to the guide shaft 16 in this fashion, the movable tank 7 (including the standoff 8) is allowed produce a linear motion as stated above. The transducer 5 is disposed within the hermetically sealed standoff 25, facing the reflecting surface 25A of the standoff 25, so that the transducer 5 can transmit and receive ultrasonic signals. One end of the transducer 5 is fixed to the fixing base. With the individual transducers 4, 5 arranged in the above-described manner, the transducers 4, 5 can detect ultrasonic signals which are emitted by their respective counterparts and pass through the ultrasound-transmitting fluid (water) and the standoffs 8, 25, and can also receive ultrasonic signals reflected by the reflecting surfaces 8A, 8B of the standoff 8 and the reflecting surface 25A of the standoff 25, respectively.

Figure 5:
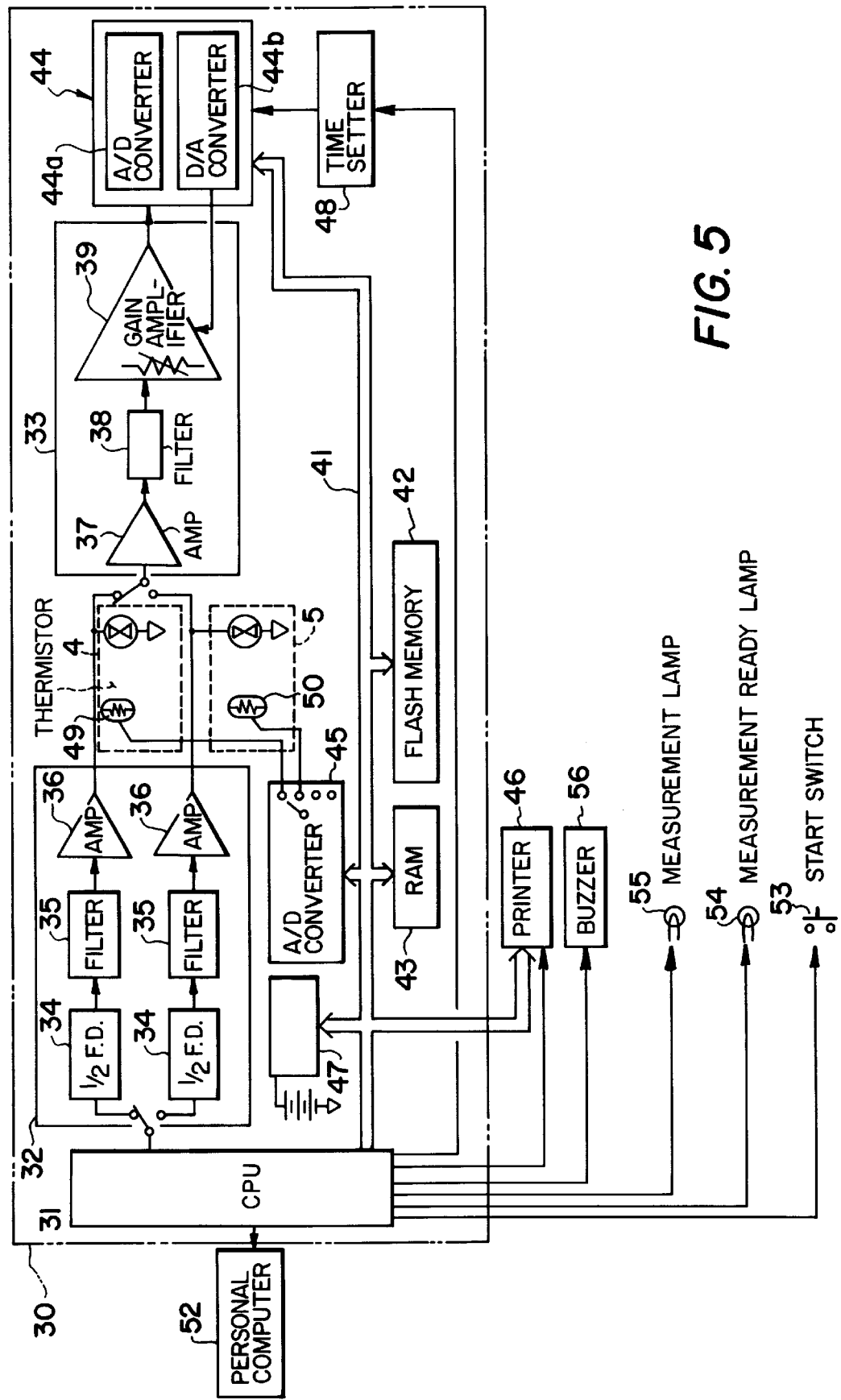
FIG. 5 is a block diagram showing a configuration for the control of the ultrasonic diagnostic apparatus.

Referring now to FIG. 5, the controller of the individual transducers 4, 5 is described. Including a central processing unit (CPU) 31, the controller 30 controls operation of the transducers 4, 5 and serves the function of carrying out later-described measurement mode, judgment mode and calibration mode in accordance with a specified program. A transmitting circuit 32 and a receiving circuit 33 are provided since the transducers 4, 5 are switched between transmission and reception. The transmitting circuit 32 comprises frequency dividers 34, filters 35 for shaping signals into a desired waveform and amplifiers 36, through which outputs are delivered to the respective transducers 4, 5. With this circuit configuration, one of the transducers 4, 5 whichever selected by the CPU 31 emits an ultrasonic signal.

The individual transducers 4, 5 are switchably connected to the receiving circuit 33. The receiving circuit 33 comprises an amplifier 37 for amplifying a received ultrasonic signal selectively entered from the transducers 4 or 5, a filter 38 for removing noise and an amplifier 39 for performing signal amplification, and is connected to a converter 44. The converter 44 includes an A/D converter 44a which digitizes the received ultrasonic signal and permits the CPU 31 to take in a resultant digitized signal as received ultrasound data and a D/A converter 44b which outputs a signal for correcting the amplification factor of the amplifier 39 of the receiving circuit 33.

The CPU 31 is connected to a flash memory 42, a RAM 43, the converter 44, a converter 45, a printer 46 and a real-time clock 47 via a bus 41 so that the CPU 31 itself functions as a microcomputer. The flash memory 42 stores a program concerning a procedure for calculating the propagation velocity of ultrasound which passes through the body part to be examined. The RAM 43 temporarily stores necessary data and allows the data to be read whenever it is required for calculating the propagation velocity. The converter 44 is for obtaining the received ultrasound data required, of which propagation delay time is measured by means of a time setter 48. The converter 45 A/D-converts outputs from temperature sensors 49, 50 provided for measuring the temperature of the ultrasound-transmitting substance surrounding the ultrasound transmitting/receiving elements 4, 5. The real-time clock 47 allows the printer 46 to print out date, for instance.

The CPU 31 is further connected to a start switch 53 which allows an operator to enter a command for stating measurement, a measurement ready lamp 54 for annunciating the operator of a measurement ready state, a measurement lamp 55 for annunciating the operator that a measurement is being made, a buzzer 56 for annunciating the operator of an end of measurement, mode alteration, and so forth, the aforementioned time setter 48, as well as a personal computer 52 which is used when taking in patient data or carrying out additional functions.

Figure 6:
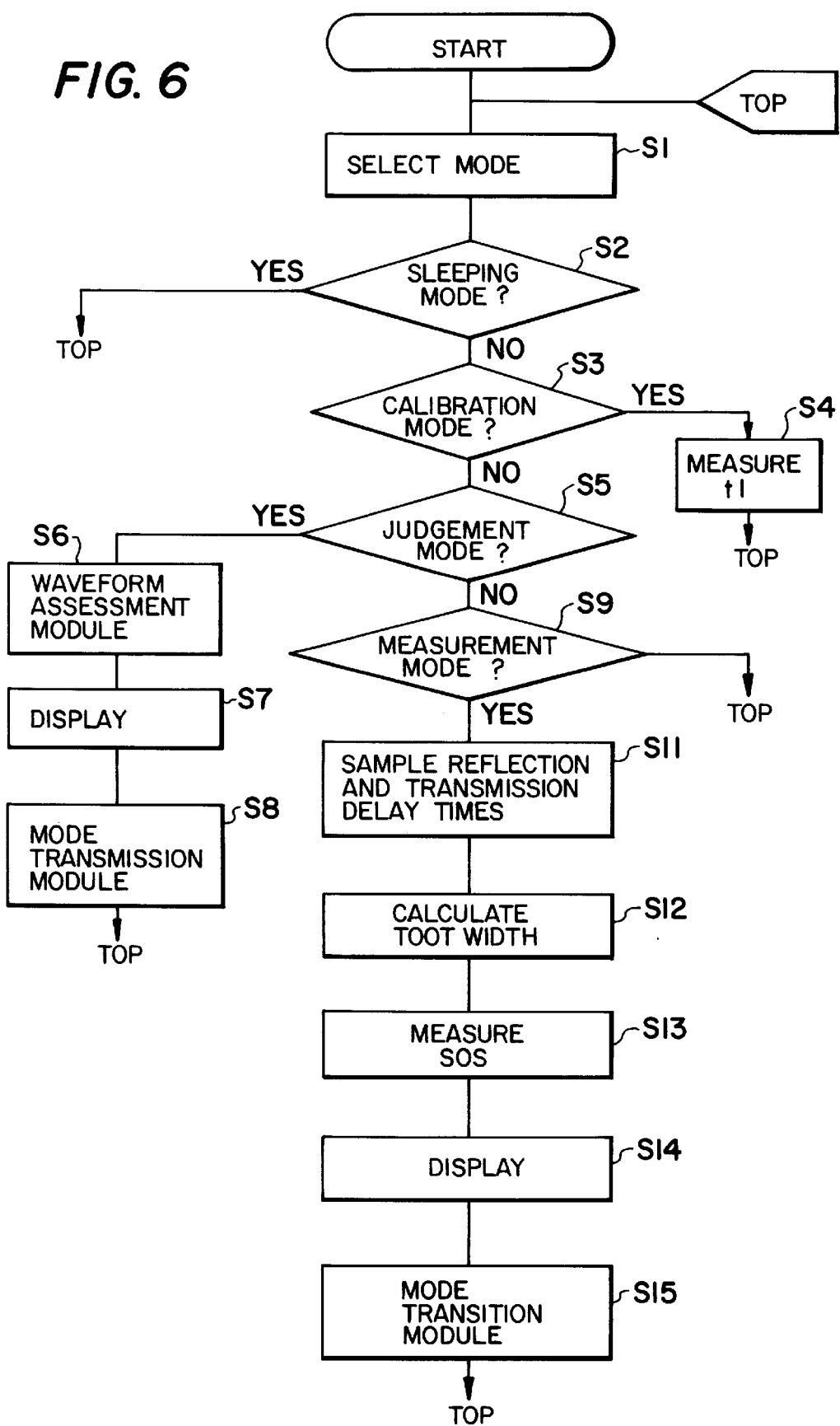
FIG. 6 is a flowchart showing a procedure of measurement to be followed by the ultrasonic diagnostic apparatus.

The procedure performed under the control of the CPU 31 in accordance with the program stored in the flash memory 42 is now discussed specifically based on a flowchart of FIG. 6. The discussion begins with a description of a concept underlying overall operation flow.

The operation flow represented in FIG. 6 includes four modes. The first mode is sleeping mode in which the apparatus 1 is kept in a standby, or idle, state; the second mode is calibration mode in which the total length of the standoffs 8 and 25 is measured with an ultrasound-transmitting object (phantom) of a known width, which is susceptible to deterioration with time, sandwiched between them; the third mode is judgment mode in which a judgment is made as to whether or not the standoffs 8 and 25 have been pushed against a heel in a proper condition; and the fourth mode is measurement mode in which the SOS is calculated.

While the second, or calibration, mode is executed only when the need arises, the other modes are repeatedly carried out in ordinary measuring operation. Thus, an automatic transition function is incorporated between the first, or sleeping, mode and the third, or judgment, mode and the fourth, or measurement, mode. Transition from the sleeping mode to the judgment mode, and to the measurement mode, is automatically made by sensing conditions in each mode.

The procedure is now described in specific detail using the flowchart of FIG. 6. First, a desired mode is selected by human operation (S1). If the second, or calibration, mode is to be selected, the calibration mode is specified by an operator input. One of the following conditions usually occurs and, in this case, the aforementioned automatic transition function is activated and selects the judgment mode:

(1) A sensor senses that the moving mechanism 10 has been operated in a direction in which the distance between the measuring units decreases.

(2) A condition in which the distance between the standoffs 8 and 25 has reaches a specified value is sensed by monitoring the movement of the standoff 8 of the movable tank 7 in terms of the travel time of reflected waves.

(3) A condition in which a foot has been placed on the platform (examination table) 9 is sensed.

Figure 8A:
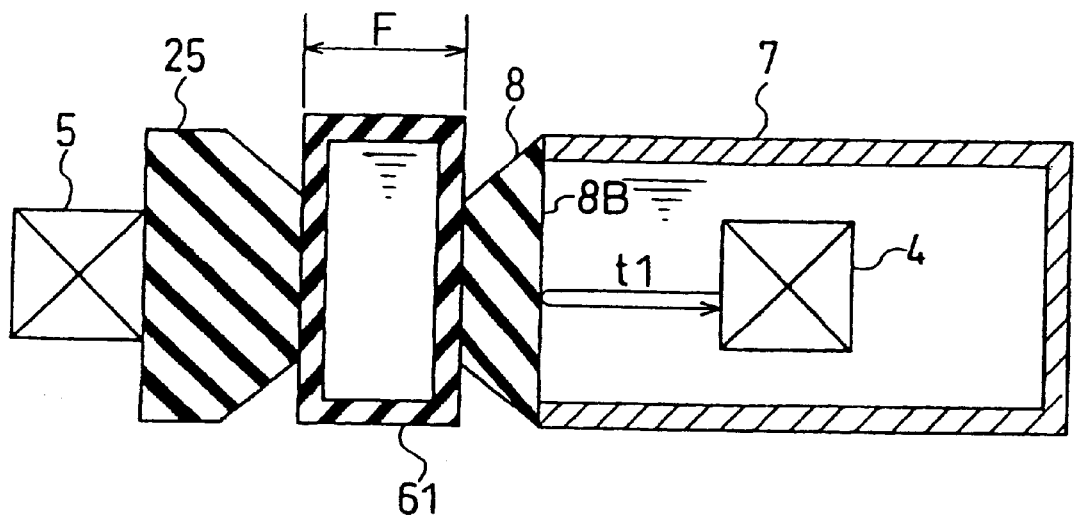
FIG. 8 is a schematic representation of measuring conditions in calibration mode and measurement mode.

If the calibration mode is selected or automatic mode transition is selected, the sleeping mode is automatically canceled (NO in S2). Then, a judgment is made to determine whether or not to execute the calibration mode (S3). When executing the calibration mode (YES in S3), time t1 is measured with the phantom sandwiched between the standoffs 8 and 25 as shown in FIG. 8(a) to obtain data corresponding to the total length of the standoffs 8 and 25 (S4) and, then, the operation flow returns to TOP.

When not executing the calibration mode (NO in S3), the operation flow proceeds to execute the judgment mode (YES in S5), and a waveform assessment module judges whether the waveform is acceptable or unacceptable (S6). The heel is usually coated with jelly to ensure proper transmission of ultrasound via the standoffs 8, 25. If, however, the amount of jelly is insufficient or the standoffs 8, 25 are not adequately pushed against the heel, an abnormal waveform is observed. Such abnormal waveforms are detected based on judgment criteria including at least signal intensity, signal waveform and signal stability through the lapse of time of each ultrasonic signal as shown in FIG. 7. The signal intensity is judged satisfactory if the maximal value of the amplitude of an ultrasonic signal sample is equal to or higher than a specified level, whereas the signal intensity is judged insufficient if the maximal value of the amplitude is lower than a specified level. (2) Also, the signal waveform is judged satisfactory if the period and interval between successive maximal values of the amplitude of the aforementioned ultrasound sample meet specified criteria, whereas the signal waveform is judged unsatisfactory if the period and interval between successive maximal values of the amplitude does not conform to the specified criteria. (3) Further, the signal is judged stable (acceptable) if a series of times at which three voltage values of the aforementioned ultrasound sample are obtained shows certain stability, whereas the signal is judged unsatisfactory if the series of times fluctuates.

The result of waveform judgment is presented by printing it out by the printer 46 and/or annunciating it by the measurement ready lamp 54 (S7), and the operation flow proceeds to execute a mode transition module (S8). The mode transition module permits the operation flow to proceed to the succeeding measurement mode when all items of FIG. 7 have been completed (NO in S5). On the other hand, the mode transition module annunciates an anomaly and returns the flow to the sleeping mode in case of failure to go through all the items of FIG. 7 within a given period of time (YES in S2). In this case, the operator checks for any cause of the anomaly and reexecutes the flow.

If the signal waveform is judged satisfactory, the operation flow automatically proceeds to the measurement mode (YES in S9). In case the mode transition module (S8) is not incorporated, the measurement mode (S9) is selected by human operation. In the measurement mode, data such as reflection delay time and transmission delay time are sampled (S11), the width of the foot is calculated based on the obtained data (S12), and then the SOS is calculated (S13). The result is presented by printing it out by the printer 46 and an end-of-measurement is annunciated by the buzzer 56 or the measurement ready lamp 54 (S14), and the operation flow proceeds to the mode transition module (S15). The mode transition module automatically returns the flow to the sleeping mode.

Figure 8B:
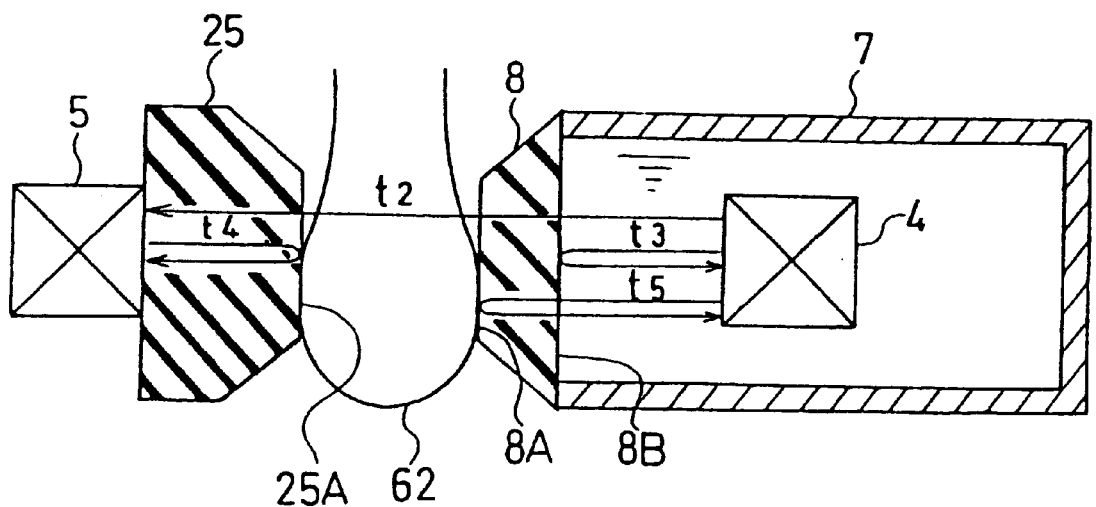

A specific example of SOS calculation in the calibration mode (S3) and the measurement mode (S9) is now described with reference to FIG. 8. FIG. 8(a) shows a condition in the calibration mode while FIG. 8(b) shows a condition in the measurement mode. The phantom (ultrasound-transmitting object) 61 of the known width F coated with jelly is sandwiched between the standoffs 8 and 25 as shown in FIG. 8(a), and reflection delay time t1 of sound waves reflected by the inside reflecting surface 8B of the standoff 8 is measured by using the movable ultrasound transmitting/receiving element 4. Next, a heel 62 coated with jelly is sandwiched between the standoffs 8 and 25 as shown in FIG. 8(b), in which reflection delay times t3 and t5 of sound waves reflected by the inside and outside reflecting surfaces 8B and 8A of the standoff 8 are measured by using the movable ultrasound transmitting/receiving element 4, reflection delay time t4 of sound waves reflected by the outside reflecting surface 25A of the standoff 25 is measured by using the fixed ultrasound transmitting/receiving element 5, and transmission delay time t2 of transmitted sound waves is measured by using the ultrasound transmitting/receiving elements 4 and 5.

The SOS can be calculated as follows:

$$\text{SOS (speed of sound)} = \text{(foot width)}/\text{(travel time)} = ((\text{position of standoff during calibration}) - (\text{position of standoff during measurement}) + (\text{width of calibration phantom}))/((\text{transmission delay time}) - (\text{reflection delay times on both sides})/2) = (F + V(Cr) \cdot t1 - V(C) \cdot t3)/(t2 - (t4 + t5)/2) \qquad (1)$$

where

F=width of phantom

V(C)=sound velocity in liquid at temperature C

C=temperature during measurement

Cr=temperature during calibration

Although the examination procedure becomes complex if the phantom is used in the calibration mode for determining the total width of the standoffs 8 and 25, it becomes possible to conduct an accurate examination even when the widths of the standoffs 8 and 25 have changed with the lapse of time. It is possible to carry out calibration operation even when the front ends of the standoffs 8 and 25 coated with jelly are brought into close contact with each other without using the phantom, because the only consequence of such arrangement is that it zeroes the value of F in equation (1). The distance to be traveled by the movable tank 7 becomes longer in this case, tough.

It is however essential to accurately measure the temperature of an ultrasound-transmitting liquid and use a liquid having such properties that permit accurate measurement of sound velocity at a given temperature because the above calculation requires the sound velocity V(C) in the liquid at temperature C. In these circumstances, a measuring method which does not require the sound velocity V(C) in the liquid is described referring to FIG. 9.

Figure 9A:
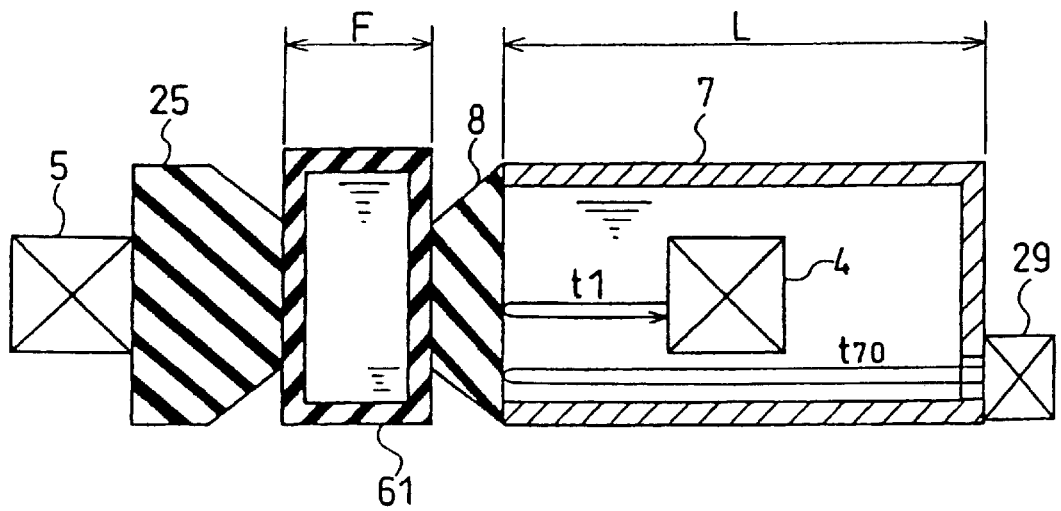
FIG. 9 is a schematic representation of measuring conditions in calibration mode and measurement mode performed by using a third ultrasound transmitting/receiving element.
Figure 9B:
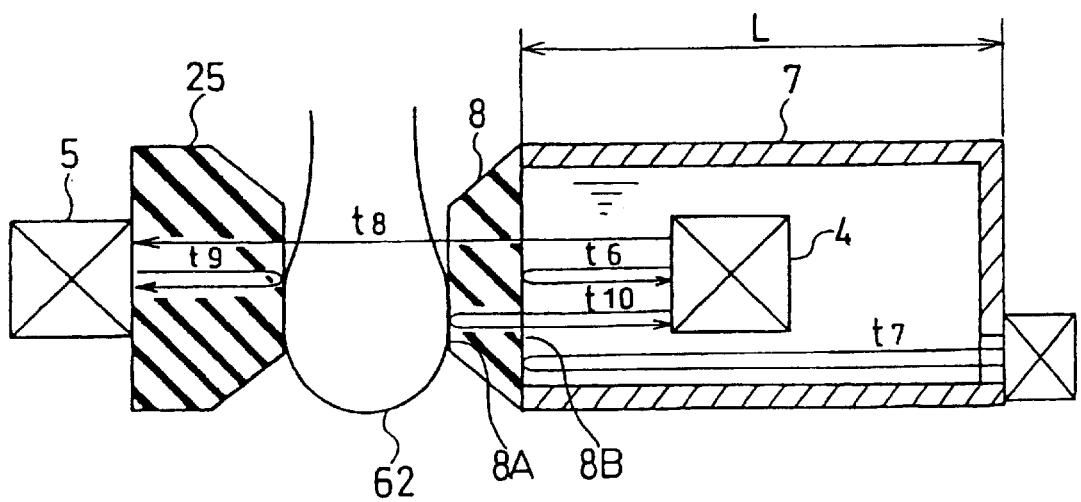

FIG. 9(a) shows a condition in the calibration mode while FIG. 9(b) shows a condition in the measurement mode. They differ from FIG. 8 in that a third ultrasound transmitting/receiving element 29 is additionally mounted at the rear end of the movable tank 7. The phantom 61 of the known width F coated with jelly is sandwiched between the standoffs 8 and 25 as shown in FIG. 9(a), and reflection delay time t1 of sound waves reflected by the inside reflecting surface 8B of the standoff 8 is measured by using the movable ultrasound transmitting/receiving element 4. Next, the heel 62 coated with jelly is sandwiched between the standoffs 8 and 25 as shown in FIG. 9(b), in which reflection delay times t6 and t10 of sound waves reflected by the inside and outside reflecting surfaces 8B and 8A of the standoff 8 are measured by using the movable ultrasound transmitting/receiving element 4, reflection delay time t9 of sound waves reflected by the outside reflecting surface 25A of the standoff 25 is measured by using the fixed ultrasound transmitting/receiving element 5, transmission delay time t8 of transmitted sound waves is measured by using the ultrasound transmitting/receiving elements 4 and 5, and reflection delay time t7 of sound waves reflected by the inside reflecting surface 8B of the standoff 8 is measured by using the fixed ultrasound transmitting/receiving element 29.

The SOS can be calculated as follows in a manner similar to the aforementioned equation (1):

$$\text{SOS (speed of sound)}=(\text{foot width})/(\text{travel time})=((\text{position of standoff during calibration})-(\text{position of standoff during measurement})+(\text{width of calibration phantom}))/((\text{transmission delay time})-(\text{reflection delay times on both sides})/2)=(F+L\cdot t1/t70-L\cdot t6/t7)/(t8-(t9+t10)/2) \quad (2)$$

where

F=width of phantom (known)

L=length of movable tank (cylinder) (known)

If the movable tank 7 is manufactured to length L with high precision and the third ultrasound transmitting/receiving element 29 is provided as described above, it is no longer needed to measure the temperature of ultrasound-transmitting liquid and it becomes possible to conduct an accurate examination, although electric circuitry becomes somewhat complicated.

Figure 10:
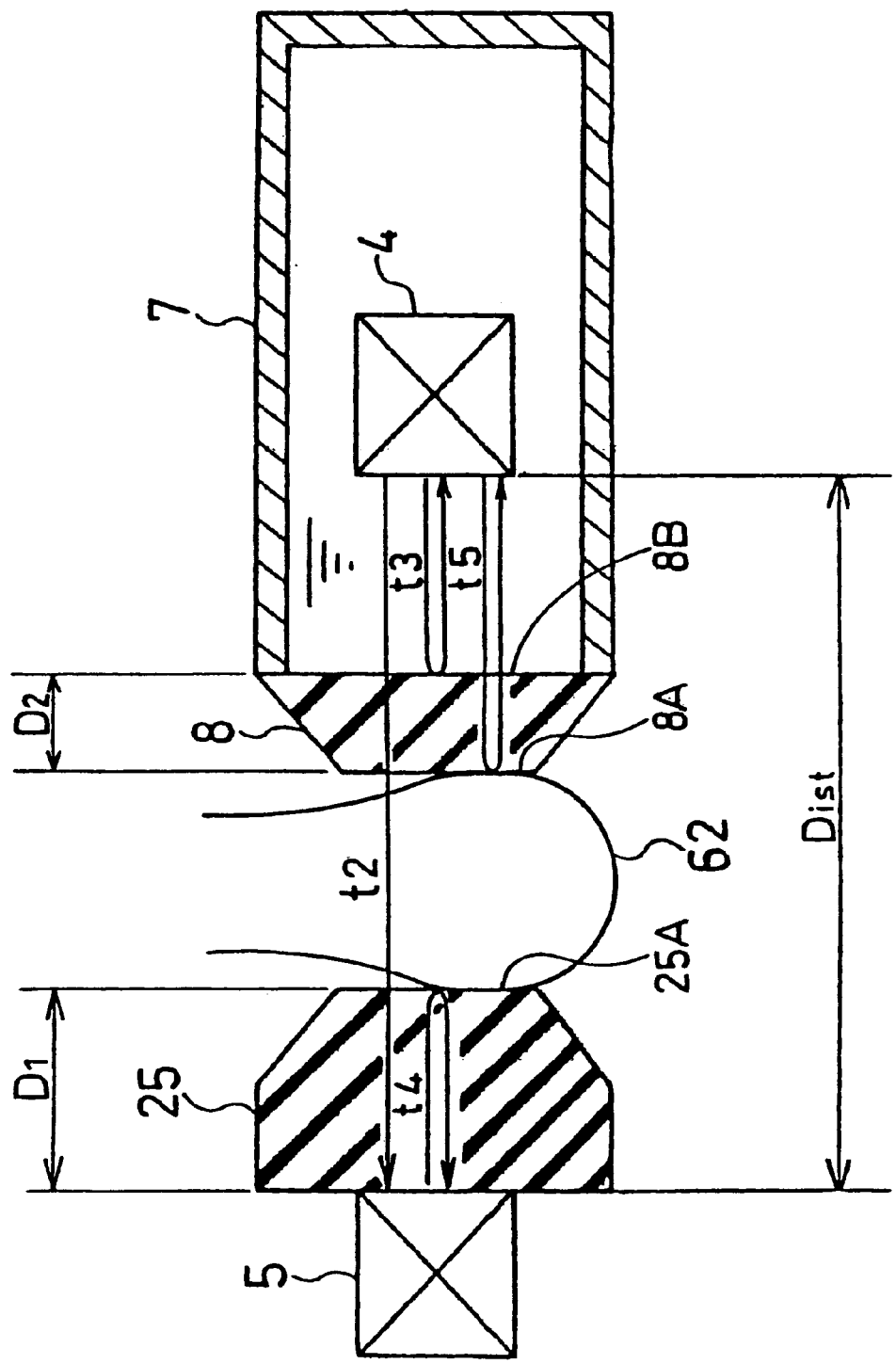
FIG. 10 is a schematic representation of a measuring condition in measurement mode without employing calibration mode.

While the foregoing discussion of the embodiment has dealt with the procedure in which the calibration mode (S3) is absolutely required, it is possible to eliminate the calibration mode (S3) if the widths of the standoffs 8 and 25 can be measured. A measurement procedure complying with this requirement is described referring to FIGS. 10 and 11. FIG. 11 differs from FIG. 10 in that a third ultrasound transmitting/receiving element 29 is additionally mounted at the rear end of the movable tank 7. In the arrangements of FIGS. 10 and 11, the widths D2 and D1 of the standoffs 8 and 25 are theoretically obtained from the following equations if urethane or other material used in the standoffs 8 and 25 is known:

$$D1=U(C)\cdot t4/2 \quad (3)$$

$$D2=U(C)\cdot (t5-t3)/2 \quad (4)$$

where

U(C)=sound velocity within standoff at temperature C

C=To be obtained with a temperature sensor or by using equation L/t7 if the third ultrasound transmitting/receiving element 29 is available.

In the case of FIG. 10, the heel 62 coated with jelly is sandwiched between the standoffs 8 and 25, and reflection delay times t3 and t5 of sound waves reflected by the inside and outside reflecting surfaces 8B and 8A of the standoff 8 are measured by using the movable ultrasound transmitting/receiving element 4, reflection delay time t4 of sound waves reflected by the outside reflecting surface 25A of the standoff 25 is measured by using the fixed ultrasound transmitting/receiving element 5, and transmission delay time t2 of transmitted sound waves is measured by using the ultrasound transmitting/receiving elements 4 and 5. Then, the SOS can be calculated by the following equation:

$$\text{SOS (speed of sound)}=(\text{foot width})/(\text{travel time})=((\text{distance between probes})-(\text{width of standoffs})-(\text{travel distance through liquid}))/((\text{transmission delay time})-(\text{reflection delay times on both sides})/2)=\text{SOS}=(\text{Dist}-D1-D2-V(C)\cdot t3/2)/(t2-(t4+t5)/2) \quad (5)$$

where

Dist=distance between probes

D1=width of standoff 25

D2=width of standoff 8

V(C)=sound velocity in liquid at temperature C

C=temperature during measurement

In the case of FIG. 11, the heel 62 coated with jelly is sandwiched between the standoffs 8 and 25, and reflection delay time t6 of sound waves reflected by the inside reflecting surfaces 8B of the standoff 8 are measured by using the movable ultrasound transmitting/receiving element 4, reflection delay time t9 of sound waves reflected by the outside reflecting surface 25A of the standoff 25 is measured by using the fixed ultrasound transmitting/receiving element 5, transmission delay time t8 of transmitted sound waves is measured by using the ultrasound transmitting/receiving elements 4 and 5, and reflection delay time t7 of sound waves reflected by the inside reflecting surface 8B of the standoff 8 is measured by using the fixed ultrasound transmitting/receiving element 29. Then, the SOS can be calculated by the following equation in a similar way to equation (5):

$$\text{SOS}=(\text{Dist}-D1-D2-L\cdot t6/t7)/(t8-(t9+t10)/2) \quad (6)$$

where

Dist=distance between probes (known)

L=length of movable tank (cylinder) (known)

The aforementioned SOS is determined by the Young's modulus and density of an object. Generally, the Young's modulus increases as the density of bone increases and, thus, sound waves propagate at a higher velocity if the bone has low elasticity. This follows that dense bones have larger SOS values. Accordingly, the SOS serves as an index which reflects both the bone density and elasticity. While the foregoing description of the embodiment has dealt with the cases in which the amount of bone mass is determined from SOS measurements, the amount of bone mass may be determined from broad ultrasound attenuation (BUA) obtained from the inclination of slopes of transmitted wave spectrum, or from the lunar stiffness index which is a mathematical index obtained from a combination of the SOS and BUA.

Data on propagation delay time, or the time that elapses between transmission and reception of an ultrasonic signal projected from each of the transducers 4, 29 and reflected by the inside reflecting surface 8B of the standoff 8, is measured in the ultrasonic diagnosis method of the embodiment. This method is used so that the ultrasonic signal is reflected by such part of the standoff 8 that is less susceptible to potential deformation the standoff 8 which is pushed against human heels. This may be varied such that the ultrasonic signal projected from each of the transducers 4, 29 is reflected by the outside reflecting surface 8A of the standoff 8. Although the measuring unit 3 is fixed in the ultrasonic diagnostic apparatus of this embodiment, the invention is not limited to this construction. The measuring unit 3 may also be made movable by constructing it with a standoff 8 and a movable tank 7 like the measuring unit 2. Furthermore, the ultrasound-transmitting liquid stored in the movable measuring unit need not necessarily be a liquid of a single kind, but a multilayer configuration having a plurality of tank sections partitioned along the direction in which ultrasound is transmitted. In this case, it is possible to employ a combination of liquids which will maintain a fixed speed of sound regardless of temperature changes.

We claim:

1. An ultrasonic diagnostic apparatus for diagnosing a characteristic of a body part to be examined by passing ultrasound through the body part to be examined comprising:

a platform on which the body part to be examined is loaded, a pair of measuring units mounted on the platform, at least one of the measuring units being made movable so that the distance between them can be varied in accordance with the size of the body part to be examined whereby the ultrasound is allowed to pass through the body part to be examined and the measuring units can be pushed against it, an ultrasound-transmitting fluid filled in the measuring unit whichever is made movable, and a pair of ultrasound transmitting/receiving elements disposed individually in the pair of measuring units, wherein the ultrasound transmitting/receiving element housed in the measuring unit whichever is made movable is held in the ultrasound-transmitting fluid and sustained by the platform such that the distance between the ultrasound transmitting/receiving elements is fixed.

2. An ultrasonic diagnostic apparatus as claimed in claim 1, wherein the measuring unit whichever is made movable includes a standoff made of an ultrasound-transmitting solid which is pushed against the body part to be examined and a movable tank fitted with the standoff at a forward end, the movable tank holding the ultrasound-transmitting fluid and accommodating the ultrasound transmitting/receiving element, with a surface of the standoff closer to the movable tank being formed to act as a reflecting surface for the ultrasound emitted from the ultrasound transmitting/receiving element.

3. An ultrasonic diagnostic apparatus as claimed in claim 2, wherein the platform is provided with a guide mechanism extending in the moving direction of the movable tank, and the guide mechanism movably supports the movable tank and immovably supports the ultrasound transmitting/receiving element.

4. An ultrasonic diagnostic apparatus as claimed in claim 3, wherein the guide mechanism has seal members fitted at least at two positions of the movable tank, a supporting point of the ultrasound transmitting/receiving element is located in a space sealed by the seal members, and the ultrasound-transmitting fluid in the movable tank is sealed off from outside air.

5. An ultrasonic diagnostic apparatus as claimed in claim 4, wherein the space sealed by the seal members is filled with the ultrasound-transmitting fluid.

6. An ultrasonic diagnostic apparatus as claimed in claim 2, wherein a third ultrasound transmitting/receiving element is attached to the rear end of the movable tank in such a way that the third ultrasound transmitting/receiving element can emit ultrasound toward and receive it from the reflecting surface of the standoff.

7. An ultrasonic diagnostic apparatus as claimed in claims 1 or 2, wherein one of the pair of measuring units is fixed while the other is made movable.

8. An ultrasonic diagnostic apparatus as claimed in claim 7, wherein the fixed measuring unit is formed of a standoff made of an ultrasound-transmitting solid which is pushed against the body part to be examined and the ultrasound transmitting/receiving element is affixed to this standoff.

9. An ultrasonic diagnostic apparatus as claimed in claim 1 further comprising a controller for controlling the pair of measuring units, wherein the controller incorporates, in addition to measurement mode in which the propagation speed of the ultrasound passing through the body part to be examined is determined from the time required for the ultrasound to pass through the body part and the width of the body part, judgment mode in which a judgment is made as to whether the ultrasound passed through the body part is acceptable or unacceptable before determining its propagation speed through the body part and/or calibration mode in which an ultrasound-transmitting object of a known width is sandwiched between the pair of measuring units, or the pair of measuring units are brought into mutual contact and the positional relationship between the measuring unit whichever is made movable and the ultrasound transmitting/receiving element housed in it is measured.

10. An ultrasonic diagnostic apparatus for diagnosing a characteristic of a body part to be examined by passing ultrasound through the body part to be examined, the ultrasonic diagnostic apparatus comprising:

a pair of ultrasound transmitting/receiving elements immovably installed facing each other to transmit and receive ultrasonic signals, a standoff mounted at the front of a transmitting/receiving surface of one of the ultrasound transmitting/receiving elements, a movable tank fitted with a standoff at a forward end, the movable tank holding an ultrasound-transmitting fluid and accommodating the other ultrasound transmitting/receiving element, and moving means for moving the movable tank either forward or backward.

11. An ultrasonic diagnostic apparatus for diagnosing a characteristic of a body part to be examined by passing ultrasound through the body part to be examined comprising:

a pair of ultrasound transmitting/receiving elements immovably installed facing each other to transmit and receive ultrasonic signals, a first standoff mounted at the front of a transmitting/receiving surface of one of the ultrasound transmitting/receiving elements, a movable tank fitted with a second standoff at a forward end, the movable tank holding an ultrasound-transmitting fluid and accommodating the other ultrasound transmitting/receiving element, moving means for moving the movable tank such that a front end surface of the first standoff and a front end surface of the second standoff are pushed against the body part to be examined which is located between the two front end surfaces, and processing means for calculating the SOS through the body part based on the signals transmitted and received by the pair of ultrasound transmitting/receiving elements.

12. An ultrasonic diagnostic apparatus for diagnosing a characteristic of a body part to be examined by passing ultrasound through the body part to be examined comprising:

a pair of ultrasound transmitting/receiving elements immovably installed facing each other to transmit and receive ultrasonic signals, a first standoff mounted at the front of a transmitting/receiving surface of one of the ultrasound transmitting/receiving elements, a movable tank fitted with a second standoff at a forward end, the movable tank holding an ultrasound-transmitting medium and accommodating the other ultrasound transmitting/receiving element, moving means for moving the movable tank such that a front end surface of the first standoff and a front end surface of the second standoff are pushed against the body part to be examined which is located between the two front end surfaces, width measuring means for measuring the width of the body part to be examined, transmission delay time measuring means for measuring the time required for an acoustic signal to pass through the body part to be examined, and processing means for calculating the SOS through the body part based on outputs of the width measuring means and the transmission delay time measuring means.

13. An ultrasonic diagnostic apparatus for diagnosing a characteristic of a body part to be examined by passing ultrasound through the body part to be examined comprising:

first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, with the second standoff having a front end surface and a rear end surface which are parallel to each other, and with the movable tank holding an ultrasound-transmitting fluid and accommodating the second ultrasound transmitting/receiving element, moving means for moving the movable tank such that the front end surface of the first standoff and the front end surface of the second standoff are pushed against a calibration phantom or the body part to be examined whichever located between the two front end surfaces, and processing means for performing a mathematical operation defined by the following equation based on signals transmitted and received by the first and second ultrasound transmitting/receiving elements:

$$SOS=(\text{width of body part})/(\text{travel time})=((\text{position of standoff during calibration})-(\text{position of standoff during measurement})+(\text{width of calibration phantom}))/((\text{transmission delay time})-(\text{reflection delay times on both sides})/2)=(F+V(Cr)\cdot t1-V(C)\cdot t3)/(t2-(t4+t5)/2)$$

where

F=width of phantom

V(C)=sound velocity in liquid at temperature C

V(Cr)=sound velocity in liquid at temperature Cr

C=temperature during measurement

Cr=temperature during calibration t1=period of time from transmission to reception of a signal emitted by the second ultrasound transmitting/receiving element and reflected by the rear end surface of the second standoff during calibration t2=period of time from transmission to reception of a signal emitted by the second ultrasound transmitting/receiving element and received by the first ultrasound transmitting/receiving element during measurement t3=period of time from transmission to reception of a signal emitted by the second ultrasound transmitting/receiving element and reflected by the rear end surface of the second standoff during measurement t4=period of time from transmission to reception of a signal emitted by the first ultrasound transmitting/receiving element and reflected by the front end surface of the first standoff during measurement t5=period of time from transmission to reception of a signal emitted by the second ultrasound transmitting/receiving element and reflected by the front end surface of the second standoff during measurement.

14. An ultrasonic diagnostic apparatus for diagnosing a characteristic of a body part to be examined by passing ultrasound through the body part to be examined comprising:

first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, with the second standoff having a front end surface and a rear end surface which are parallel to each other, and with the movable tank holding an ultrasound-transmitting fluid and accommodating the second ultrasound transmitting/receiving element, moving means for moving the movable tank such that the front end surface of the first standoff and the front end surface of the second standoff come into mutual contact during calibration or the front end surface of the first standoff and the front end surface of the second standoff are pushed against the body part to be examined which is located between the two front end surfaces during measurement, and processing means for performing a mathematical operation defined by the following equation based on signals transmitted and received by the first and second ultrasound transmitting/receiving elements:

$$SOS=(\text{width of body part})/(\text{travel time})=(V(Cr)\cdot t1-V(C)\cdot t3)/(t2-(t4+t5)/2)$$

where

V(C)=sound velocity in liquid at temperature C

V(Cr)=sound velocity in liquid at temperature Cr

C=temperature during measurement

Cr=temperature during calibration t1=period of time from transmission to reception of a signal emitted by the second ultrasound transmitting/receiving element and reflected by the rear end surface of the second standoff during calibration t2=period of time from transmission to reception of a signal emitted by the second ultrasound transmitting/receiving element and received by the first ultrasound transmitting/receiving element during measurement t3=period of time from transmission to reception of a signal emitted by the second ultrasound transmitting/ receiving element and reflected by the rear end surface of the second standoff during measurement t4=period of time from transmission to reception of a signal emitted by the first ultrasound transmitting/receiving element and reflected by the front end surface of the first standoff during measurement t5=period of time from transmission to reception of a signal emitted by the second ultrasound transmitting/receiving element and reflected by the front end surface of the second standoff during measurement.

15. An ultrasonic diagnostic apparatus for diagnosing a characteristic of a body part to be examined by passing ultrasound through the body part to be examined comprising:

first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, with the second standoff having a front end surface and a rear end surface which are parallel to each other, and with the movable tank holding an ultrasound-transmitting fluid and accommodating the second ultrasound transmitting/receiving element, a third ultrasound transmitting/receiving element installed at a read end of the movable tank, moving means for moving the movable tank such that the front end surface of the first standoff and the front end surface of the second standoff are pushed against a calibration phantom or the body part to be examined whichever located between the two front end surfaces, and processing means for performing a mathematical operation defined by the following equation based on signals transmitted and received by the first, second and third ultrasound transmitting/receiving elements:

$$SOS=(\text{width of body part})/(\text{travel time})=((\text{position of standoff during calibration})-(\text{position of standoff during measurement})+(\text{width of calibration phantom}))/((\text{transmission delay time})-(\text{reflection delay times on both sides})/2)=(F+L \cdot t1/t70-L \cdot t6/t7)/(t8-(t9+t10)/2)$$

where

F=width of phantom

L=length of movable tank t1=period of time from transmission to reception of a signal emitted by the second ultrasound transmitting/receiving element and reflected by the rear end surface of the second standoff during calibration t6=period of time from transmission to reception of a signal emitted by the second ultrasound transmitting/receiving element and reflected by the rear end surface of the second standoff during measurement t7=period of time from transmission to reception of a signal emitted by the third ultrasound transmitting/receiving element and reflected by the rear end surface of the second standoff during measurement t8=period of time from transmission to reception of a signal emitted by the second ultrasound transmitting/receiving element and received by the first ultrasound transmitting/receiving element during measurement t9=period of time from transmission to reception of a signal emitted by the first ultrasound transmitting/receiving element and reflected by the front end surface of the first standoff during measurement t10=period of time from transmission to reception of a signal emitted by the second ultrasound transmitting/receiving element and reflected by the front end surface of the second standoff during measurement t70=period of time from transmission to reception of a signal emitted by the third ultrasound transmitting/receiving element and reflected by the rear end surface of the second standoff during calibration.

16. An ultrasonic diagnostic apparatus for diagnosing a characteristic of a body part to be examined by passing ultrasound through the body part to be examined comprising:

first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, with the second standoff having a front end surface and a rear end surface which are parallel to each other, and with the movable tank holding an ultrasound-transmitting fluid and accommodating the second ultrasound transmitting/receiving element, moving means for moving the movable tank such that the front end surface of the first standoff and the front end surface of the second standoff are pushed against the body part to be examined which is located between the two front end surfaces, and processing means for performing a mathematical operation defined by the following equation based on signals transmitted and received by the first and second ultrasound transmitting/receiving elements:

$$SOS=(\text{width of body part})/(\text{travel time})=((\text{distance between probes})-(\text{width of standoffs})-(\text{travel distance through liquid}))/((\text{transmission delay time})-(\text{reflection delay times on both sides})/2)=(\text{Dist}-D1-D2-V(C) \cdot t3/2)/(t2-(t4+t5)/2)$$

where

Dist=distance between first and second ultrasound transmitting/receiving elements D1=width of first standoff D2=width of second standoff V(C)=sound velocity in liquid at temperature C C=temperature during measurement t2=period of time from transmission to reception of a signal emitted by the second ultrasound transmitting/receiving element and received by the first ultrasound transmitting/receiving element t3=period of time from transmission to reception of a signal emitted by the second ultrasound transmitting/receiving element and reflected by the rear end surface of the second standoff t4=period of time from transmission to reception of a signal emitted by the first ultrasound transmitting/receiving element and reflected by the front end surface of the first standoff t5=period of time from transmission to reception of a signal emitted by the second ultrasound transmitting/receiving element and reflected by the front end surface of the second standoff.

17. An ultrasonic diagnostic apparatus for diagnosing a characteristic of a body part to be examined by passing ultrasound through the body part to be examined comprising:

first and second ultrasound transmitting/receiving elements immovably installed facing each other to transmit and receive ultrasonic signals, a first standoff having a front end surface and mounted at the front of a transmitting/receiving surface of the first ultrasound transmitting/receiving element, a movable tank fitted with a second standoff at a forward end, with the second standoff having a front end surface and a rear end surface which are parallel to each other, and with the movable tank holding an ultrasound-transmitting fluid and accommodating the second ultrasound transmitting/receiving element, a third ultrasound transmitting/receiving element installed at a read end of the movable tank, moving means for moving the movable tank such that the front end surface of the first standoff and the front end surface of the second standoff are pushed against the body part to be examined which is located between the two front end surfaces, and processing means for performing a mathematical operation defined by the following equation based on signals transmitted and received by the first, second and third ultrasound transmitting/receiving elements:

$$SOS = (\text{width of body part})/(\text{travel time}) = (\text{Dist} - D1 - D2 - L \cdot t6/t7)/(t8 - (t9 + t10)/2)$$

where

Dist=distance between first and second ultrasound transmitting/receiving elements D1=width of first standoff D2=width of second standoff t6=period of time from transmission to reception of a signal emitted by the second ultrasound transmitting/receiving element and reflected by the rear end surface of the second standoff t7=period of time from transmission to reception of a signal emitted by the third ultrasound transmitting/receiving element and reflected by the rear end surface of the second standoff t8=period of time from transmission to reception of a signal emitted by the second ultrasound transmitting/receiving element and received by the first ultrasound transmitting/receiving element t9=period of time from transmission to reception of a signal emitted by the first ultrasound transmitting/receiving element and reflected by the front end surface of the first standoff t10=period of time from transmission to reception of a signal emitted by the second ultrasound transmitting/receiving element and reflected by the front end surface of the second standoff.

18. An ultrasonic diagnostic apparatus as claimed in each of claims 10 through 17, wherein the ultrasound-transmitting medium is fluid.

* * * * *

UNITED STATES PATENT AND TRADEMARK OFFICE
CERTIFICATE OF CORRECTION

PATENT NO.    : 5,944,665  Page 1 of 1
DATED         : August 31, 1999
INVENTOR(S)   : Iino et al.

It is certified that error appears in the above-identified patent and that said Letters Patent is hereby corrected as shown below:

Title page,
Item [22], change filing date from "Aug. 8, 1997" to -- Aug. 4, 1997 --

Signed and Sealed this

Nineteenth Day of August, 2003

JAMES E. ROGAN
*Director of the United States Patent and Trademark Office*